(12) United States Patent
Prestegarden

(10) Patent No.: US 9,353,156 B2
(45) Date of Patent: May 31, 2016

(54) OLIGOPEPTIDE COMPOUNDS AND USES THEREOF

(71) Applicant: Cytovation AS, Bergen (NO)

(72) Inventor: Lars Prestegarden, Bergen (NO)

(73) Assignee: Cytovation AS, Bergen (NO)

(*) Notice: Subject to any disclaimer, the term of this patent is extended or adjusted under 35 U.S.C. 154(b) by 0 days.

(21) Appl. No.: 14/305,743

(22) Filed: Jun. 16, 2014

(65) Prior Publication Data

US 2015/0038407 A1 Feb. 5, 2015

Related U.S. Application Data

(63) Continuation of application No. 13/574,124, filed as application No. PCT/EP2011/051422 on Feb. 1, 2011, now Pat. No. 8,754,042.

(30) Foreign Application Priority Data

Feb. 1, 2010 (GB) .................................. 1001602.0

(51) Int. Cl.
| | | |
|---|---|---|
| *C07K 14/00* | (2006.01) | |
| *C07K 7/08* | (2006.01) | |
| *C07K 14/47* | (2006.01) | |
| *A61K 38/16* | (2006.01) | |
| *A61K 45/06* | (2006.01) | |

(52) U.S. Cl.
CPC ................. *C07K 14/00* (2013.01); *A61K 38/16* (2013.01); *A61K 45/06* (2013.01); *C07K 7/08* (2013.01); *C07K 14/4703* (2013.01)

(58) Field of Classification Search
CPC ....... A61K 38/16; A61K 45/06; C07K 14/00; C07K 14/4703; C07K 7/08
See application file for complete search history.

(56) References Cited

U.S. PATENT DOCUMENTS

| | | | |
|---|---|---|---|
| 5,595,756 | A | 1/1997 | Bally et al. |
| 5,656,122 | A | 8/1997 | Lenz et al. |
| 6,080,724 | A | 6/2000 | Chassaing et al. |
| 6,472,507 | B1 | 10/2002 | Fischer et al. |
| 6,645,501 | B2 | 11/2003 | Dowdy |
| 7,307,143 | B1 | 12/2007 | Behrens et al. |
| 8,754,042 | B2 | 6/2014 | Prestegarden |
| 2013/0023461 | A1 | 1/2013 | Prestegarden |

FOREIGN PATENT DOCUMENTS

| | | |
|---|---|---|
| WO | WO91/01891 | 2/1991 |
| WO | WO00/29427 | 5/2000 |
| WO | WO2004/069279 | 8/2004 |
| WO | WO2008/051048 | 5/2008 |
| WO | WO2008/070325 | 6/2008 |

OTHER PUBLICATIONS

Håvard Jenssen, Peptide Antimicrobial Agents, Clinical Microbiology Reviews, Jul. 2006, p. 491-511.*
Auerbach, "Angiogenesis assays: Problems and Pitfalls," Cancer and Metastasis Reviews. vol. 19 pp. 167-172 (2002).
Baker et al., "Anticancer Efficacy of Magainin2 and Analogue Peptides," Cancer Research. vol. 53 pp. 3052-3057 (1993).
Beekman, Jeffrey M. et al., "Modulation of Fc Periplakin", J. Biol. Chem., 2004, vol. 279 pp. 33875-33881.
Berendsen, "A glimpse of the Holy Grail?" Science. vol. 282 pp. 642-643 (1998).
Bradley, C.M., and Barrick, D., "Limits of Cooperativity in a Structurally Modular Protein: Response of the Notch Ankyrin Domain to Analogous Alanine Substitutions in Each Repeat," J. Mol. Biol. vol. 324 pp. 373-386 (2002).
Chen et al., "RGD-Tachyplesin Inhibits Tumor Growth," Cancer Research. vol. 61 pp. 2434-2438 (2001).
Chen et al., "Selective killing of transformed cells by cyclin/cyclin-dependent kinase 2 antagonists", Proc. Natl. Acad. Sci. U.S.A., 1999, vol. 96, pp. 4325-4329.
Dadiani et al., "High-Resolution Magnetic Resonance Imaging of Disparities in the Transcapillary Transfer Rates in Orthotopically Inoculated Invasive Breast Tumors," Cancer Research. vol. 64 pp. 3155-3161 (2004).
de Coupade et al., "Novel human-derived cell-penetrating peptides for specific subcellular delivery of therapeutic biomolecules," Biochem. J. vol. 390 pp. 407-418 (2005).
De Lucca, A.J., and Walsh, T.J., "Antifungal peptides: Origin, activity, and therapeutic potential," Rev. Iberoam. Micol. vol. 17 pp. 116-120 (2000).
Dings et al., "The Designed Angiostatic Peptide Anginex Synergistically Improves Chemotherapy and Antiangiogenesis Therapy with Angiostatin," Cancer Research. vol. 63 pp. 382-385 (2003).
EBI Database Accession No. ARL94496, "Conductin RGS domain protein (78-200)," (1 page) (Jul. 23, 2009).
Ellerby et al., "An Artificially Designed Pore-forming Protein with Anti-tumor Effects," The Journal of Biological Chemistry. vol. 278, No. 37 pp. 35311-35316 (2003).
Ellerby et al., "Anti-cancer activity of targeted pro-apoptotic peptides," Nature Medicine. vol. 5, No. 9 pp. 1032-1038 (1999).
Elliott, G., and O'Hare, P., "Intercellular Trafficking and Protein Delivery by a Herpesvirus Structural Protein," Cell. vol. 88 pp. 223-233 (1997).
Elmquist, A. and Langel, Ü., "In vitro Uptake and Stability Study of pVEC and Its All-D Analog," Biol. Chem. vol. 384 pp. 387-393 (2003).
Epand, R.M., and Vogel, H.J., "Diversity of antimicrobial peptides and their mechanisms of action," Biochimica et Biophysica Acta. vol. 1462 pp. 11-28 (1999).
Friedrich, "Antibacterial Action of Structurally Diverse Cationic Peptides of Gram-Positive Bacteria," Antimicrobial Agents and Chemotherapy. vol. 44, No. 8 pp. 2086-2092 (2000).
Gura, "Systems for Identifying New Drugs Are Often Faulty," Science. vol. 278, No. 5340 pp. 1041-1042 (1997).

(Continued)

*Primary Examiner* — James H Alstrum Acevedo
*Assistant Examiner* — Erinne Dabkowski
(74) *Attorney, Agent, or Firm* — Jenkins, Wilson, Taylor & Hunt, P.A.

(57) ABSTRACT

The present invention relates to novel agents, pharmaceutical compositions containing them, and their use in therapy, particularly anti-microbial and anti-cancer therapy. In particular, the present invention relates to novel peptide-based compounds based on SEQ ID NO: 40 which have surprisingly been shown to have inhibitory effects on the growth and/or viability of cells, particularly bacterial and cancer cells. Also provided are therapeutic and non-therapeutic methods which include the use of peptides of the invention.

18 Claims, 10 Drawing Sheets

(56) References Cited

OTHER PUBLICATIONS

Hancock, "Peptide antibiotics," The Lancet. vol. 349 pp. 418-422 (1997).
Holm et al., "Uptake of cell-penetrating peptides in yeasts," FEBS Letters. vol. 579 pp. 5217-5222 (2005).
Jain, "Barriers to Drug Delivery in Solid Tumors," Scientific American. vol. 271, No. 1 pp. 58-65 (1994).
Järver, P., and Langel, Ü., "Cell penetrating peptides—A brief introduction," Biochemica et Biophysica Acta. vol. 1758 pp. 260-263 (2006).
Kondo et al., "Highly efficient delivery of p16 antitumor peptide into aggressive leukemia/lymphoma cells using a novel transporter system," Molecular Cancer Therapeutics. vol. 3, No. 12 pp. 1623-1630 (2004).
Krauss et al., "In vitro gene delivery by a novel human calcitonin (hCT)-derived carrier peptide," Bioorganic & Medicinal Chemistry Letters. vol. 14 pp. 51-54 (2004).
Landon, "Rational design of peptides active against the gram positive bacteria *Staphylococcus aureus*," Proteins. vol. 72 pp. 229-239 (2008).
Leuschner et al., "Membrane disrupting lytic peptide conjugates destroy hormone dependent and independent breast cancer cells in vitro and in vivo," Breast Cancer Research and Treatment. vol. 78 pp. 17-27 (2003).
Liu et al., "Perforin: structure and function," Immunology Today. vol. 16, No. 4 pp. 194-201 (1995).
Mabjeesh et al., "2ME2 inhibits tumor growth and angiogenesis by disrupting microtubules and dysregulating HIF," Cancer Cell. vol. 3 pp. 363-375 (2003).
Manno et al., "Identification of a functional role for lipid asymmetry in biological membranes: Phosphatidylserine-skeletal protein interactions modulate membrane stability," PNAS. vol. 99, No. 4 pp. 1943-1948 (2002).
Matz et al., "Fluorescent proteins from nonbioluminescent Anthozoa species," Nature Biotechnology. vol. 17 pp. 969-973 (1999).
Miller, James H. et al., "The dimerization domain of HIV-1 viral infectivity factor Vif is required to block virion incorporation of APOBEC3G", Retrovirology, 2007, vol. 4: 81, pp. 1-11.
Mocellin et al., "Cancer vaccine development: on the way to break immune tolerance to malignant cells," Experimental Cell Research. vol. 299 pp. 267-278 (2004).
Muhle, S.A., and Tam J.P., "Design of Gram-Negative Selective Antimicrobial Peptides," Biochemistry. vol. 40, No. 19 pp. 5777-5785 (2001).
Neidle, "Cancer Drug Design and Discovery," Elsevier/Academic Press. pp. 427-431 (2008).
Ngo et al., "Computational Complexity, Protein Structure Prediction, and the Levinthal Paradox," The Protein Folding Problem and Tertiary Structure Prediction. pp. 491-494 (1994).
Notice of Allowance corresponding U.S. Appl. No. 13/574,124 dated Feb. 5, 2014.
Notification Concerning Transmittal of International Preliminary Report on Patentability.(Chapter I of the Patent Cooperation Treaty) corresponding to International Patent Application No. PCT/EP2011/051422 dated Aug. 16, 2012.
Notification of Transmittal of the International Search Report and the Written Opinion of the International Searching Authority, or the Declaration corresponding to International Patent Application No. PCT/EP2011/051422 dated Jun. 15, 2011.
Oehlke et al., "Cellular uptake of an α-helical amphipathic model peptide with the potential to deliver polar compounds into the cell interior non-endocytically," Biochimica et Biophysica Acta. vol. 1414 pp. 127-139 (1998).
Official Action corresponding to Japanese Patent Application No. 2012-550478 dated Mar. 24, 2015. (Translation).
Official Action corresponding to U.S. Appl. No. 13/574,124 dated Apr. 17, 2013.
Official Action corresponding to U.S. Appl. No. 13/574,124 dated Jan. 29, 2013.
Ohsaki et al., "Antitumor Activity of Magainin Analogues against Human Lung Cancer Cell Lines," Cancer Research. vol. 52 pp. 3534-3538 (1992).
Orzáez et al., "Conjugation of a novel Apaf-1 inhibitor to peptide-based cell-membrane transporters: Effective method to improve inhibition of mitochondria-mediated apoptosis," Peptides. vol. 28, No. 5 pp. 358-368 (2007).
Papo et al., "A Novel Lytic Peptide Compsed of DL-Amino Acids Selectively Kills Cancer Cells in Cluture and in Mice, " The Journal of Biological Chemistry. vol. 278, No. 23 pp. 21018-21023.
Papo et al., "Suppression of Human Prostate Tumor Growth in Mice by a Cytolytic D-, L-Amino Acid Peptide: Membrane Lysis, Increased Necrosis, and Inhibition of Prostate-Specific Antigen Secretion," Cancer Research. vol. 64 pp. 5779-5786 (2004).
Papo et al., "The Consequence of Sequence Alteration of an Amphipathic (-Helical Antimicrobial Peptide and Its Diastereomers," The Journal of Biological Chemistry. vol. 277, No. 37 pp. 33913-33921 (2002).
Papo, N., and Shai, Y., "New Lytic Peptides Based on the D,L-Amphipathic Helix Motif Preferentially Kill Tumor Cells Compared to Normal Cells," Biochemistry. vol. 42, No. 31 pp. 9346-9354 (2003).
Patel et al., "CL1-GFP: An Androgen Independent Metastatic Tumor Model for Prostate Cancer," The Journal of Urology. vol. 164 pp. 1420-1425 (2000).
Pettit et al., "Antineoplastic Agents. 565. Synthesis of Combretastatin D-2 Phosphate and Dihydro-combretastatin D-2," J. Nat. Prod. vol. 72, No. 5 pp. 876-883 (2009).
Pooga et al., "Cell penetration by transportan," FASEB Journal. vol. 12 pp. 67-77 (1998).
Potocky, et al., "Cytoplasmic and Nuclear Delivery of a TAT-derived Peptide and a β-Peptide after Endocytic Uptake into HeLa Cells" The Journal of Biological Chemistry. vol. 278, No. 50 pp. 50188-50194 (2003).
Pujals, S., and Giralt, E., "Proline-rich, amphipathic cell-penetrating peptides," Advanced Drug Delivery Reviews. vol. 60 pp. 473-484 (2008).
Rosenfield et al., "Endotoxin (Lipopolysaccharide) Neutralization by Innate Immunity Host-Defense Peptides: Peptide Properties and Plausible Modes of Action," The Journal of Biological Chemistry. vol. 281, No. 3 pp. 1636-1643 (2006).
Rothbard et al., "Conjugation of arginine oligomers to cyclosporine A facilitates topical delivery and inhibition of inflammation," Nature Medicine. vol. 6, No. 11 pp. 1253-1257 (2000).
Rousselle et al., "New Advances in the Transport of Doxorubicin through the Blood-Brain Barrier by a Peptide Vector-Mediated Strategy," Molecular Pharmacology. vol. 57 pp. 679-686 (2000).
Rudinger, "Characteristics of the amino acids as components of a peptide hormone sequence," Peptide Hormones. Chapter 1, J.A. Parsons. Ed. pp. 1-7 (1976).
Salzet, "Neuropeptide-Derived Antimicrobial Peptides from Invertebrates for Biomedical Applications," Current Medicinal Chemistry. vol. 12, No. 26 pp. 3055-3061 (2005).
Snyder et al., "Treatment of Terminal Peritoneal Carcinomatosis by a Transducible p53-Activating Peptide," PLoS Biology. vol. 2 pp. 0186-0193 (2004).
Soomets et al., "Deletion analoguesof transportan," Biochimica et Biophysica Acta. vol. 1467 pp. 165-176 (2000).
Sporn, M.B., and Suh, N., "Chemoprevention of cancer," Carcinogenesis. vol. 21, No. 3 pp. 525-530 (2000).
Sramkoski et al., "A New Human Prostate Carcinoma Cell Line, 22Rv1," In Vitro Cell. Dev. Biol.—Animal. vol. 35 pp. 403-409 (1999).
Street et al., "Perforin and interferon-γ activities independently control tumor initiation, growth, and metastasis," Blood. vol. 97 pp. 192-197 (2001).
Vivés et al., "A Truncated HIV-1 Tat Protein Basic Domain Rapidly Translocates through the Plasma Membrane and Accumulates in the Cell Nucleus," The Journal of Biological Chemistry. vol. 272, No. 25 pp. 16010-16017 (1997).
Voet, D., and Voet, J.G., "Biochemistry," 2nd Edition. Chapter 9, Section 9-3. Abnormal Hemoglobins. John Wiley & Sons, Inc.: New York pp. 235-241 (1995).

(56) References Cited

OTHER PUBLICATIONS

Wagstaff, K.M., and Jans, D.A., "Protein Transduction: Cell Penetrating Peptides and Their Therapeutic Applications," Current Medicinal Chemistry. vol. 13 pp. 1371-1387 (2006).

Wyman et al., "Design, Synthesis, and Characterization of a Cationic Peptide That Binds to Nucleic Acids and Permeabilizes Bilayers," Biochemistry. vol. 36, No. 10 pp. 3008-3017 (1997).

Zwaal et al., "Surface exposure of phosphatidylserine in pathological cells," Cellular and Molecular Life Sciences. vol. 62 pp. 971-988 (2005).

Zwaal, R.F.A., and Schroit, A.J., "Pathophysiologic Implications of Membrane Phospholipid Asymmetry in Blood Cells," Blood. vol. 89, No. 4 pp. 1121-1132 (1997).

"Designing Custom Peptides," SIGMA. (2 pages) (Accessed on Dec. 16, 2004).

* cited by examiner

A

B

OLIGOPEPTIDE COMPOUNDS AND USES THEREOF

RELATED APPLICATIONS

This application is a continuation of U.S. patent application Ser. No. 13/574,124, filed Jul. 19, 2012, now U.S. Pat. No. 8,754,042; which is a National Stage Entry of PCT International Patent Application Serial No. PCT/EP2011/051422, filed Feb. 1, 2011; which itself claimed the benefit of GB 1001602.0, filed Feb. 1, 2010. The disclosure of each of these applications is incorporated herein by reference in its entirety.

The present invention relates to novel agents, pharmaceutical compositions containing them, and their use in therapy, particularly anti-microbial and anti-cancer therapy. In particular, the present invention relates to novel peptide-based compounds which have surprisingly been shown to have inhibitory effects on the growth and/or viability of cells, particularly bacterial and cancer cells. The new peptides of the invention have been shown to have cytotoxic effects on bacterial and cancer cells and to inhibit the growth of tumours. Such peptides, or mimetics thereof, may thus be used in the therapy of cancer or as anti-microbial agents, more particularly as anti-tumour or anti-bacterial agents. Also provided are therapeutic and non-therapeutic methods which comprise the use of peptides of the invention.

Cancer is a condition in which cells display uncontrolled growth and intrusion on and destruction of adjacent tissues. In some cases the cancer cells metastasize and travel to other locations, forming secondary sites of cancer. Cancer affects people at all ages, with the risk for most types increasing with age. Cancer caused about 13% of all human deaths in 2007 (7.6 million). Indeed, annually 600, 000 people die from cancer in the US alone.

Cancers are caused by abnormalities in the genetic material of cells. These abnormalities may be due to the effects of carcinogens, such as tobacco smoke, radiation, chemicals, or infectious agents. Other cancer-promoting genetic abnormalities may randomly occur through errors in DNA replication, or are inherited, and thus present in all cells from birth. The heritability of cancers is usually affected by complex interactions between carcinogens and the host's genome.

It is known that the human immune system may recognize and destroy cancer cells, mainly through receptor-mediated mechanisms (1-3). However, despite immune surveillance, cancer cells can evade host immunological control, and thus surgical intervention or treatment of the cancer is usually necessary.

Due to research and advances in medicine, the majority of cancers can be treated in some form, and a smaller number of cancers can be cured, depending on the specific type, location, and stage. Once diagnosed, cancer is usually treated with a combination of surgery, chemotherapy and radiotherapy. However, a large number of cancers cannot currently be cured by traditional methods, and thus alternative treatments for cancer patients are needed. Host immunological control is often mediated by host defence-derived cytolytic cationic polypeptides and this, amongst other things, has led to the proposal to use anti-cancer peptides in the treatment of cancer. Such peptides were initially discovered due to their role in clearance of bacteria (4-7). However, tumours seem to overcome these host control mechanisms via, as yet unknown, non-receptor mediated mechanisms (8-13).

It is known that peptides which exhibit an inhibitory effect against cancer cells ("inhibitory peptides") bind strongly to negatively charged membranes (4, 5, 14-18) and lysis of the membrane can ensue (19, 20). Typically many anti-cancer peptides are cationic. The plasma membrane of cancer cells contains small amounts of negatively charged phosphatidylserine (3-9%; refs. 21, 22), and cancer cells are thus slightly more negative than most non-malignant eukaryotic cells. Whether this small difference in the membrane composition provides the explanation for the ability of some cationic peptides preferentially to kill cancer cells is still not clear (23-25).

Surface-exposed phosphatidylserine also serves as a marker for the clearance of cancer cells from the bloodstream by innate immunity effectors such as monocytes, although through completely different (receptor-mediated) mechanisms (26). It has been proposed in the art that the actual destruction of tumour cells by cationic peptides is the result of one of the two processes: (i) induction of necrosis resulting from the disruption of the cytoplasmic membrane (20, 25) or (ii) induction of apoptosis triggered by the binding of the peptides to the mitochondrial membrane (9, 27). Many anti-cancer peptides described in the art are believed to exert their effects by a mechanism involving cell lysis.

Despite the potent anti-cancer activity of certain such peptides in vitro, studies in vivo are limited. At present, only a few studies have been carried out in vivo with peptides capable of disrupting cancer cell membranes and subsequently causing cancer cell death. These studies include (i) systemic treatments of solid tumours with lytic peptides, but only when they were conjugated to homing (targeting) domains or when used as propeptides (12, 27) as the lytic entity is inactivated in serum and lacks tumour specificity; (ii) treatment of ovarian cancer with magainin and its D-amino acid enantiomer, but only when injected i.p. at high doses (28); and (iii) an intra-tumour administration of a 69-amino-acid pore-forming peptide against human breast cancer xenografts (11).

All of these treatments influenced only slightly, if at all, disseminated metastases (27) because of either limited intrinsic local activity or their inability to reach sizeable metastases in the intact animals. To date, the selectivity of cytotoxic peptides for cancer cells, and their toxicity to other healthy organs, have not been extensively studied. In the case of one peptide, however, namely D-K6L9, a short 15-mer D,L-amino acid peptide, it has been shown that intra-tumoural injection inhibits the growth of primary human prostate carcinomas without affecting the non-malignant neighboring cells (13). It has been shown in mice that peptide D-K6L9 specifically targets and inhibits the growth of primary and metastatic tumours when administered systemically. This peptide seems to act on phosphatidylserine in the plasma membrane via depolarizing lytic mechanisms.

Thus, whilst some progress has been made in the field of anti-cancer peptides, a need still exists for new peptides which are effective at destroying or inhibiting the growth of cancer cells and which do not exhibit cytotoxicity towards non-cancerous cells.

As mentioned above, work on the development of anti-cancer peptides has principally focused on cytolytic anti-microbial peptides and a number of such peptides have been shown to act in vitro against different types of cancer cells. Such peptides have a central role in the innate immunity of organisms including insects, amphibians and mammals. Examples include human defensins, cecropins, cecropin-magainin hybrids, magainins, and such peptides conjugated to homing domains and propeptides. As discussed above, these peptides preferentially bind and disrupt negatively charged phopholipid membranes, the major component of the bacterial cytoplasmic membrane.

Microorganisms such as bacteria are the cause of many infectious diseases, and are responsible for a large number of deaths each year. For example, pathogenic bacteria cause diseases such as tuberculosis. As microorganisms are responsible for many infectious diseases, and resistance of pathogenic microorganisms is a serious problem facing modern medicine, new and alternative treatments against microorganisms are highly desirable.

The present invention addresses these needs, and provides novel peptide-based compounds as surprisingly effective new anti-cancer and anti-microbial agents.

Thus, a novel peptide has been designed and peptides based on this have surprisingly been shown to be effective against both cancer and bacterial cells in vitro and to inhibit the growth of tumours in vivo. As described in the Examples below, peptides based on this novel peptide sequence exhibited cytotoxic activity against a variety of cancer cell lines, whilst showing very low activity against normal cells and low toxicity. A cytotoxic effect was also shown against a variety of bacterial species, including both gram-positive and gram-negative bacteria. Furthermore, in animal models of cancer, a strong anti-tumour effect was observed, with a significant and marked inhibitory effect on tumour growth. Treated animals had a significant survival advantage compared to the untreated group, and indeed studies suggest that animals may be cured of their tumours. Thus, a dramatic anti-cancer, or anti-tumour, effect has been demonstrated. (In this sense "anti-cancer" is meant to mean a negative effect on cancer cells, more particularly on the growth and/or viability of cancer cells, and more particularly a cytotoxic effect on cancer cells).

The present inventors initially sought to design peptides having a "tumour suppressor" effect, based on the amino acid sequences of known tumour suppressor proteins. Thus it was hoped to design peptides which would bind to the receptors of tumour suppressor proteins and thereby block tumour growth. A panel of 96 peptides was prepared and screened for anti-cancer and anti-microbial activity. The peptide which underlies the present invention was identified in this screen, one of only three peptides showing significant levels of activity. The peptide of the present invention exhibited unexpectedly high cytotoxic activity towards both cancer cells and microbial cells, both in vitro and in vivo in the case of cancer cells. Surprisingly, given the rationale of the peptide library design, the peptide was found to have lytic activity, disrupting the plasma membrane of cancer cells and lysing bacteria. Furthermore, an apoptotic effect was also surprisingly observed, suggesting that the peptides may trigger or induce apoptosis. As mentioned above, further studies have shown that this anti-cancer effect may be selective for cancer cells, leaving non-cancerous cells intact, which is a significant advantage in the treatment of cancer, where the negative side-effects of treatments, for example chemotherapy treatment, are often substantial. The peptide-based compounds of the invention have also been shown to eradicate several bacterial strains, and could provide an effective tool against multi-resistant bacteria.

Based on these surprising and unpredictable results, the present inventors now propose that peptides and peptide-based compounds based on this novel peptide sequence, namely the sequence of SEQ ID NO. 1:

KTLRVAKAIYKRYIE (SEQ ID NO:1)

may be used therapeutically in the treatment of cancer and microbial infections, and more generally also as anti-microbial agents, encompassing also non-therapeutic uses, for example to combat microbial contamination or colonisation, e.g. as a disinfectant etc.

Accordingly, in one aspect the present invention provides an oligopeptidic compound comprising:

(i) all or part of the amino acid sequence of SEQ ID NO. 1; or (ii) an amino acid sequence having at least 85% sequence identity to SEQ ID NO:1; or (iii) an amino acid sequence which is all or part of the reverse sequence of SEQ ID NO: 1 (namely all or part of SEQ ID NO: 2: EIYRKYIAKAVRLTK) or which is the reverse sequence of an amino acid sequence having at least 85% sequence identity to SEQ ID NO:1;

wherein the compound has activity in (i.e. is capable of or is effective in) inhibiting the growth and/or viability of cancer and/or microbial cells. Alternatively put the compound may have anti-tumour or anti-microbial activity, in the case of the latter, preferably anti-bacterial activity.

As will be described in more detail below, the oligopeptidic compounds of the invention may advantageously be provided with an additional oligopeptidic sequence having "cell-penetrating" activity (as defined further below). In particular, such cell-penetrating oligopeptidic sequences based on the HIV-TAT peptide are preferred. A peptide designed on this basis is investigated in the Examples below and has been shown to be particularly efficacious.

Accordingly, in a preferred aspect the present invention provides an oligopeptidic compound comprising:

(i) all or a part of the amino acid sequence YGRKKRRQR-RRGKTLR VAKAIYKRYIE (SEQ ID NO: 40); or (ii) an amino acid sequence having at least 85% sequence identity to the sequence of SEQ ID NO:40; or (iii) an amino acid sequence which is all or part of the reverse sequence of SEQ ID NO. 40 (namely all or part of SEQ ID NO. 41 EIYRKYIAKAVRLTK GRRRQR-RKKRGY) or which is the reverse sequence of an amino acid sequence having at least 85% sequence identity to the sequence of SEQ ID NO:40 wherein the compound has activity in (i.e. is capable of or is effective in) inhibiting the growth and/or viability of cancer and/or microbial cells. Alternatively put the compound may have anti-tumour or anti-microbial activity, in the case of the latter, preferably anti-bacterial activity.

The oligopeptidic compound of SEQ ID NO:40 corresponds to the HIV-TAT sequence of SEQ ID NO:36 (see further below) joined to the N-terminal end of SEQ ID NO:1.

The oligopeptidic compounds of the invention thus have an inhibitory effect on the growth and/or viability of cells, particular cancer or microbial cells, especially bacteria. The compounds thus have cytostatic or cytotoxic activity, preferably cytotoxic activity, particularly against cancer or microbial cells, e.g. against tumours. In one aspect the compounds are bacteriostatic or bacteriocidal, preferably bacteriocidal.

"Inhibiting the growth" of a cell means that any aspect of the growth of the cell, be that an increase in the size of a cell or in the amount and/or volume of its constituents, but more particularly an increase in the numbers of a cell, is reduced, more particularly measurably reduced. The term "growth" thus explicitly includes replication or reproduction of a cell. The rate of growth of a cell, e.g. in terms of the rate in increase of cells numbers may be reduced. By way of representative example, growth (e.g. cell numbers, or rate of growth) may be reduced by at least 50, 60, 70, 80, 90 or 95%. In certain cases, growth may be reduced by 100% i.e. growth ceases or is completely inhibited. Thus replication, or reproduction of the cell may be reduced or inhibited. Thus the term "inhibit" includes any degree of reduction of growth (as compared for example to growth which may be observed in the absence of the oligopeptidic compound). The rate of replication or reproduction may be assessed or expressed in terms of generation time, particularly in the case of microbial cells (i,e, the time it takes for the microorganism to generate a copy of itself). In terms of cancer cells, growth may be assessed by determining cell numbers or by assessing the size of a tumour or its rate of growth.

"Inhibiting the viability" of a cell includes any effect which reduces the viability of a cell, or which renders it less likely to survive, or non-viable. The viability of a cell may be viewed as the ability of a cell to survive under given conditions. In particular it includes killing or destroying a cell i.e. causing it to die. Death may be assessed by failure to grow, including to replicate, or to utilise or assimilate nutrients, or by morphological changes to the cell, or the tissue in which the cell is contained e.g. the tumour, for example necrosis may be evident. Typically, a cell can be considered dead if cell membrane integrity is lost.

The terms "cytostatic" and "cytotoxic" may be analagously interpreted.

Methods for determining the viability or growth of cancer or microbial cells are well-known in the art. Many routine assays are available to determine if a cell is alive (viable) or dead. One option is to place the cell in conditions that would normally support the growth of that cell and monitor the growth of the cell by appropriate standard means, e.g. by monitoring the size of the cell, the morphology of the cell, the number of cells over time, the consumption of nutrients in the culture media, etc. Another option is to assess the cell for morphologies characteristic of cell death, e.g. necrotic or apoptotic bodies, membrane blebs, nuclear condensation and cleavage of DNA into regularly sized fragments, ruptured cell walls or membranes and leakage of cell contents into the extracellular environment.

Other methods exploit the characteristic loss of cell membrane integrity in dead cells. Membrane impermeable dyes (e.g. trypan blue and propidium iodide) are routinely used to assess membrane integrity. These dyes are excluded from intact cells and so no staining occurs in such cells. If cell membrane integrity is compromised, these dyes can access the cells and stain intracellular components. Alternatively, or in addition, dyes that only stain cells with intact membranes are used to give an indication of the viability of the cell. The Live/Dead Assay of Invitrogen Ltd is an assay that uses two dyes, one to stain dead cells, the other to stain live cells. Another approach to assessing membrane integrity is to detect the release of cellular components into the culture media, e.g. lactate dehydrogenase.

A still further option is to measure the metabolism of the cell. This can be done routinely in a number of ways. For instance the levels of ATP can be measured. Only living cells with intact membranes can synthesis ATP and because ATP is not stored in cells, levels of ATP drop rapidly upon cell death. Monitoring ATP levels therefore gives an indication of the status of the cell. A yet further option is to measure the reducing potential of the cell. Viable cells metabolising nutrients use reducing reactions and accordingly by applying a marker that gives different outputs whether in reduced or oxidised form (e.g. a fluorescent dye) to the cell, the reducing potential of the cell can be assessed. Cells that lack the ability to reduce the marker can be considered to be dead. The MTT and MTS assays are convenient examples of this type of assay.

An "anti-tumour" effect or activity may be seen as an effect on the growth and/or viability of a tumour. The term includes any negative effect or activity on the tumour. The cells of the tumour may be killed or destroyed. The growth of the tumour may be inhibited, for example the tumour may fail to grow or the rate of growth of the tumour may be reduced (for example as compared with the tumour prior to treatment with the compound, or with an equivalent or corresponding untreated tumour). The size of the tumour may reduce, or in advantageous situations the tumour may disappear altogether (i.e. be ablated or destroyed). An anti-tumour effect may in certain cases include an effect in reducing the spread of cancer cells from the tumour, e.g. the metastatic potential of the tumour may be reduced. Other pathogenic properties or behaviour of the tumour may also be reduced, for example its ability to invade or infiltrate surrounding tissues.

With reference to the definitions given above, an "antimicrobial" activity means any effect in killing or destroying, or inhibiting the growth of a microorganism, and by analogy an anti-bacterial activity is any effect in killing or destroying, or inhibiting the growth of bacteria.

Advantageously, the oligopeptidic compounds of the invention act directly on the cells i.e. they may directly inhibit growth and/or viability of the cells. By "directly" it is meant that the compounds do not recruit physiological systems or mechanisms (e.g. the immune system) to impart their effects (e.g. their cytotoxic or cytostatic effects). Rather, the compounds act directly on the cell.

In order to aid an oligopeptidic compound of the invention in exerting its effects, or to facilitate, or in certain cases to enable those effects, the compound may be provided with means to facilitate, improve or enable its delivery into cells (intracellular delivery).

Accordingly, in one embodiment, the oligopeptidic compound further comprises a cell penetrating sequence (cell penetrating peptide). In a preferred aspect of this embodiment the oligopeptidic compound comprises a cell penetrating sequence which is based on the HIV-TAT sequence, particularly amino acids 47-58.

Thus, it can be seen that in such embodiments the oligopeptidic compound of the invention may take the form of a construct containing (i.e. comprising) an oligopeptidic compound of the invention together with a cell penetrating sequence or peptide. In this aspect the invention may accordingly be seen to provide a construct comprising an oligopeptidic compound of the invention, together with at least one cell penetrating peptide. As used in the context of a "cell penetrating peptide" the term "peptide" is not limited solely to a peptide having peptide bonds, but includes also other peptide-like or peptide-based compounds e.g. peptidomimetic structures, as discussed further below. In other words a "cell penetrating peptide" may include any oligopeptidic compound having cell penetrating activity.

Thus the cell penetrating peptide may be a sequence which acts to transport the oligopeptidic compound into a cell, or across a cell membrane (i.e., into the interior of a cell). It may thus be a so-called "cell penetrating" sequence (or more particularly "cell penetrating peptide") also known in the art as a protein transduction domain (PTD) or protein transduction sequence.

Accordingly, as noted above a preferred embodiment of the invention is a construct comprising (i) an oligopeptidic compound of the invention as defined herein, and (ii) a cell penetrating sequence (more particularly a cell penetrating peptide).

Cell penetrating peptide (CPP) technology has developed greatly over recent years and a wide variety of cell penetrating peptides are known and described in the art and indeed a range of such peptides are commercially available. Cell penetrating peptides may vary greatly in size, sequence and charge, and indeed in their mechanism of function (which is presently not known for some peptides and not fully elucidated for others), but share the common ability to translocate across the plasma membrane and deliver an attached or associated moiety (the so-called "cargo") into the cytoplasm, or even in some cases the nucleus, of a cell. CPPs are thus peptide-based delivery vectors.

CPPs may be derived from naturally-occurring proteins which are able to translocate across cell membranes such as the *Drosophila* homeobox protein Antennapedia (a transcriptional factor), viral proteins such as the HIV-1 transcriptional factor TAT and the capsid protein VP22 from HSV-1, and or they may be synthetically-derived, e.g., from chimeric proteins or synthetic polypeptides such as polyarginine. As noted above, there is not a single mechanism responsible for the transduction effect and hence the design of CPPs may be based on different structures and sequences. Cell penetrating peptides are reviewed in Jarver et al. 2006 Biochimica et Biophysica Acta 1758, pages 260-263 and Table 1 below lists various representative peptides. U.S. Pat. No. 6,645,501 further describes various cell penetrating peptides which might be used.

TABLE 1

| CPP | SEQUENCE | REFERENCE |
|---|---|---|
| Antp Class | | |
| Penetratin | RQIKIWFQNRRMKWKK (SEQ ID NO: 3) | Bolton (2000) Eur. J. Neuro. 12:287 |
| Penatratin derivatives | RRMKWKK (SEQ ID NO: 4)<br>NRRMKWKK (SEQ ID NO: 5)<br>QNRRMKWKK (SEQ ID NO: 6)<br>FQNRRMKWKK (SEQ ID NO: 7)<br>RREKWKK (SEQ ID NO: 8)<br>RRQKWKK (SEQ ID NO: 9)<br>KRMKWKK (SEQ ID NO: 10)<br>RKMKWKK (SEQ D NO: 11)<br>RROKWKK (SEQ ID NO: 12)<br>RRMKQKK (SEQ ID NO: 13)<br>RRMKWFK (SEQ ID NO: 14)<br>RORKWKK (SEQ D NO: 15)<br>RRMWKKK (SEQ ID NO: 16)<br>RRMKKWK_(SEQ ID NO: 17)<br>(using standard single amino acid notation, ornithine (O), diaminobutyric acid (B), norleucine (N)) | US 6472507<br>EP4855781<br>WO 97/12912 |
| D-Penetratin | rqikiwfqnrrmkwkk (SEQ ID NO: 18) | Rouselle, C. et al. (2000) Mol. Pharm 57:679 |
| Protegrin Class | | |
| Pegelin (SynB) | RGGRLSYSRRRFSTSTGR (SEQ ID NO: 19) | Rouselle, C. et al. (2000) Mol. Pharm 57:679 |
| HIV-TAT Class | | |
| HV-TAT | GRKKRRQRRRPPQ (SEQ ID NO: 20) | Vives E. J Biol, Chem 1997, 272:16010<br>Snyder (2004) PLOS 2: 186 |
| 47-57 OF HIV-TAT | YGRKKRRQRRR (SEQ ID NO: 21) | Potocky et al. (2003) JBC |
| VP22 | DAATATRGRSAASRPTERPRAPARSASRPRRVD (SEQ ID NO: 22) | Elliott g. Cell 1997, 88:223-233 |
| Amphipathic peptides | | |
| MAP | KLALKLALKALKAALKLA (SEQ ID NO: 23) | Morris M C., Nat Biotechnol. 2001, 19:1173-1176 |
| Transportan | GWTLNSAGYLLGKINLKALAALAKKIL (SEQ ID NO: 24) | Pooga M, FASEB J 1998, 12:67-77 |

TABLE 1-continued

| CPP | SEQUENCE | REFERENCE |
|---|---|---|
| Transportan-10 | AGYLLGKINLKALAALAKKIL (SEQ ID NO: 25) | Soomets U, Biochim Biophys Acta 2000, 1467:165-176 |
| KALA | WEAKLAKALAKALAKHLAKALAKALKACEA (SEQ D NO: 26) | Oehike J., Biochim Biophys Acta 1998, 1414:127-139 |
| Pep-1 | KETWWETWWTEWSQPKKKRKV (SEQ ID NO: 27) | Wyman Biochemistry 1997, 36:3008-3017 |
| Pep-2 | KETWFETWFTEWSQPKKKRKV (SEQ ID NO: 28) | |
| MPG | GALFLGFLGAAGSTMGAWSQPKSKRKV (SEQ ID NO: 29) | Wagstaff K M Curr Med Chem 2006, 13:1371-1387 |
| Vectocell peptides | VKRGLKLRHVRPRVTRMDV (SEQ ID NO: 30)<br>SRRARRSPRHLGSG* (SEQ ID NO: 31)<br>LRRERQSRLRRERQSR* (SEQ ID NO: 32)<br>GAYDLRRRERQSRLRRRERQSR (SEQ ID NO: 33)<br>*indicates addition of cys for conjugation to cargo | Coupade (2005) Biochem. J. 407 |
| Wr-T transporter | KETWWETWWTEWWTEWSQ-GPG-rrrrrrrr (SEQ ID NO: 34)<br>r = D-enantiomer arginine | Kondo (2004) Mol. Can. Thera 1623 |
| Other peptides | | |
| R7 | RRRRRRR (SEQ ID NO: 35) | Rothbard et al., Nat. Med 6 (2000) 1253-1257 |

Sequences based on the HIV-TAT sequence and HIV-TAT and fragments thereof represent a preferred class of CPPs for use according to the present invention. Various TAT-based CPPs are described in U.S. Pat. No. 5,656,122. An exemplary HIV-TAT peptide as used in the Examples below is YGRKKRRQRRRG (SEQ ID. No. 36) and this forms a preferred aspect of the invention, but it will readily be appreciated that longer or shorter TAT fragments may be used. The amino acid sequence of HIV-TAT may be modified and/or truncated, or the peptide may be chemically-modified or retro-, inverso- or retro-inverso analogues may be made whilst retaining cell-penetrating activity.

Another group of cell penetrating peptides are Antennapedia-derived CPPs (Antp class) based around the 16 amino acid Penetratin sequence as shown in Table 1, which corresponds to the third loop of antennapedia protein and was shown to be responsible for translocation of the protein. Penetratin has been extensively developed as a delivery vehicle, including particularly for pharmaceutical use, and a wide range of Penetratin derivatives and modified sequences have been proposed and described. Reference may be made in particular to WO 91/1891, WO 00/1417, WO 00/29427, WO 2004/069279 and U.S. Pat. No. 6,080,724. Thus, the 16 amino acid sequence of Penetratin may be modified and/or truncated, or the peptide may be chemically-modified or retro-, inverso- or retro-inverso analogues may be made whilst retaining cell-penetrating activity.

As mentioned above no particular structural features or sequence motifs are common to all CPPs. However, various classes of CPPs may be identified by particular features, such as for example peptides which are amphipathic and net positively charged. Other groups of CPPs may have a structure exhibiting high α-helical content. Another group may be peptides characterised by a high content of basic amino acids. CPPs may thus be or may comprise oligomers of basic amino acids such as arginine e.g. 5 to 20, 6 to 15 or 6 to 12 R residues e.g. $R_7$ (SEQ ID NO: 35), $R_8$ (SEQ ID NO: 37) or $R_{11}$ (SEQ ID NO: 38) or $QSR_8$ (SEQ ID NO: 39).

Proline-rich amphipathic peptides are another class of CPP and such peptides characterised by the presence of pyrrolidine rings from prolines are described in Pujals et al. 2008 Advanced Drug Delivery Reviews 60, pages 473-484.

Other successfully developed CPPs include pVEC (Elmquist et al. 2003 Biol. Chem 384, pages 387-393; Holm et al. 2005 Febs Lett. 579, pages 5217-5222) and calcitonin-derived peptides (Krauss et al. 2004 Bioorg. Med. Chem. Lett., 14, pages 51-54).

Commercially available CPPs include Chariot, based on the Pep-1 peptide (Active Motif, France), the Syn-B vectors based on the protegrin peptide PG-1 (Syntem, France), and Express-si Delivery based on the MPG peptide from Genospectra, USA.

In addition to publicly available and reported CPPs, novel or derivative CPP peptides may be designed and synthesized based on known or reported criteria (e.g. known CPP sequences or features such as basic amino acid content, α-helical content etc as discussed above). Additionally, randomly-designed or other peptides may be screened for CPP activity, for example by coupling or attaching such a peptide containing a reporter molecule e.g. a detectable label or tag such as a fluorescent tag to the desired cargo (an oligopeptidic compound according to the present invention) and testing to see if the construct is translocated across the cell membrane, for example by adding these peptides to live cells followed by examination of cellular import e.g. using confocal microscopy.

Indeed, whilst it is generally the case that a CPP will penetrate or enter virtually any cell type, it may in some cases be observed that successful or efficient delivery may be dependent, or may vary depending, on the precise nature of the cargo (e.g. cargo peptide sequence) and/or the CPP used. It would be well within the routine skill of the person skilled in the art to determine optimum peptide sequences and combinations etc, and to test and/or modify cargo and/or CPP sequence or structure etc.

A representative oligopeptidic compound (or construct) of the invention may thus comprise:
(a) a first oligopeptidic sequence comprising:
  (i) all or part of the amino acid sequence of SEQ ID NO. 1; or
  (ii) an amino acid sequence having at least 85% sequence identity to SEQ ID NO:1; or
  (iii) an amino acid sequence which is all or part of the reverse sequence of SEQ ID NO. 1 (namely all or part of SEQ ID NO. 2: EIYRKYIAKAVRLTK) or which is the reverse sequence of an amino acid sequence having at least 85% sequence identity to SEQ ID NO:1; and
(b) a second oligopeptidic sequence being a cell penetrating peptide sequence.

Component (b) may be selected from any of the CPPs set out above, and more particularly any of the HIV-TAT-based or derived sequences.

The CPP (i.e. component (b) in the definition above) may be attached or provided at either the N- or the C-terminal end of the oligopeptidic compound, but preferably it is at the N-terminal end. Thus components (a) and (b) may be attached or linked in any order, but preferably in the order (a)-(b).

The components or elements of the oligopeptidic compound (or construct) according to the invention may be attached or linked to one another in any desired or convenient way according to techniques well known in the art. Thus, the components or separate parts may be linked or conjugated chemically e.g. using known chemical coupling technologies or the constructs may be formed as a single whole using genetic engineering techniques e.g. techniques for forming fusion proteins, or they may simply be synthesized as a whole e.g. using peptide synthesis techniques.

The separate parts or components may be linked directly to each other or they may be linked indirectly by means of one or more linker (or spacer) sequences. Thus, a linker sequence may interspace or separate the two parts of the compound (or the two separate components in an oligopeptidic construct). The precise nature of the linker sequence is not critical and it may be of variable length and/or sequence, for example it may have 0-15, 0-12, 0-10, 0-8, 0-6, 0-4 or 0-3 residues e.g. 1, 2 or 3 or more residues. By way of representative example the linker sequence, if present, may have 1-15, 1-12, 1-10, 1-8, 1-6 or 1-4 residues etc. The nature of the residues is not critical and they may for example be any amino acid, e.g. a neutral amino acid, or an aliphatic amino acid, or alternatively they may be hydrophobic, or polar or charged or structure-forming e.g. proline. Exemplary linker sequences thus include any single amino acid residue e.g. A, I, L, V, G, R, Q, T, or W, or a di-, tri- tetra- penta- or hexa-peptide composed of such residues.

When the oligopeptidic compound comprises a sequence which is the reverse sequence of SEQ ID NO:1 (or of a functionally-equivalent variant thereof having at least 85% sequence identity), then it is preferred that the sequence of the CPP (e.g. of component (b)) is also reversed, and that it is attached in reverse order. In other words, it is preferred that the sequence of the whole compound (or construct) comprising the two parts is reversed. However, it is not excluded that only one of the parts is reversed, or that both parts are reversed, but attached in "non-reversed" order.

A representative preferred compound of the invention may have the sequence:

```
YGRKKRRORRRGKTLRVAKAIYKRYIE    (SEQ ID NO: 40)
```

Compounds of the invention may include compounds which comprise:
(i) all or a part of the amino acid sequence of SEQ ID NO: 40; or
(ii) an amino acid sequence having at least 85% sequence identity to SEQ ID NO:40; or
(iii) an amino acid sequence which is all or part of the reverse sequence of SEQ ID NO. 40 (namely all or part of SEQ ID NO. 41 EIYRKYIAKAVRLTKGRRRQRRKKRGY) or which is the reverse sequence of an amino acid sequence having at least 85% sequence identity to SEQ ID NO:40.

A cancer cell according to the invention may be cell from any cancer, e.g. any of the cancers described below. It may be a tumour cell. The cell may be a cell in or from a clinical tumour or cancer tissue or it may a cell from a cancer cell line.

The term "microbial cell" as used herein includes any microorganism. Thus the cell may be eukaryotic or prokaryotic and includes bacteria, fungi, algae, archaea and protists. The term thus includes organisms that are typically unicellular, but which may have the capability of organising into simple cooperative colonies or structures such as filaments, hyphae or mycelia (but not true tissues) under certain conditions. The microorganism may be from any class, genus or species of microorganism. Examples of prokaryotic microorganisms include, but are not limited to, bacteria, including the mycoplasmas, (e.g. Gram-positive, Gram-negative bacteria or Gram test non-responsive bacteria) and archaeobacteria. Eukaryotic microorganisms include fungi, algae and others that are, or have been, classified in the taxonomic kingdom Protista or regarded as protists, and include, but are not limited to, for example, protozoa, diatoms, protoophyta, and fungus-like molds. The microorganism may be aerobic or anaerobic. The microorganism may be pathogenic or non-pathogenic, or a be spoilage or an indicator microorganism. In particular preferred embodiments the microorganism is pathogenic.

Multi-drug resistant organisms (MDRO) generally are bacteria that are not affected by the clinical doses of classical antibiotics. Bacteria which are resistant to three or more classes of antibiotic may generally be regarded as MDROs. The oligopeptidic compounds of the present invention may be used in the treatment or prevention of infection by MDROs, for example *Salmonella* spp., *Campylobacter* spp., *Escherichia coli*, *Staphylococcus* and *Enterococcus* spp. that are MDR. MRSA is an example of a multi-drug resistant bacteria.

In one embodiment of the invention the microbial cells are multi-drug resistant bacteria.

Bacteria or fungi represent preferred classes of microbial cell, particularly bacteria.

Examples of genera or species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfornonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania, Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactruni, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*; e.g. gram-positive bacteria such as, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides, Actinomyces israelii, Propionibacterium acnes,* and *Enterococcus* species and Gram-negative bacteria such as *Clostridium tetani, Clostridium perfringens, Clostridium botulinum, Pseudomonas aeruginosa, Vibrio cholerae, Actinobacillus pleuropneumoniae, Pasteurella haemolytica, Pasteurella multocida, Legionella pneumophila, Salmonella typhi, Brucella abortus, Chlamydi trachomatis, Chlamydia psittaci, Coxiella burnetti, Escherichia coli, Neiserria meningitidis, Neiserria gonorrhea, Haemophilus influenzae, Haemophilus ducreyi, Yersinia pestis, Yersinia enterolitica, Escherichia coli, E. hirae, Burkholderia cepacia, Burkholderia pseudomallei, Francisella tularensis, Bacteroides fragilis, Fusobascterium nucleatum, Cowdria ruminantium.*

Thus, by way of representative example, the microbial cell may be bacteria of the genus *Staphylococcus, Pseudomonas, Legionella, Mycobacterium, Proteus, Klebsiella, Fusobacterium* or other enteric or coliform bacteria.

The microbial cell may also be a, or from a, fungus, including for example fungi that may be, or may have been, classified as protista, e.g. fungi from the genera *Candida, Aspergillus, Pneumocystis, Penicillium* and *Fusarium*. Representative fungal species include, but are not limited to, *Candida albicans, Candida dubliniensis, Cryptococcus neoformans, Histoplama capsulatum, Aspergillus fumigatus, Coccidiodes immitis, Paracoccidiodes brasiliensis, Blastomyces dermitidis, Pneumocystis carnii, Penicillium marneffi, Alternaria alternate.*

The microbial cell may also be an, or from an, alga, including for example algae that may be, or may have been, classified as protista. Representative algal species include *Chaetophora, Chlorella protothecoides, Coleochaete scutata, Coleochaete soluta, Cyanidioschyzon merolae Aphanochaete, Gloeotaenium, Oedogonium, Oocystis, Oscillatoria, Paradoxia multisitia, Phormidium, Chroococcus, Aphanothece, Fragillaria, Cocconis, Navicula, Cymbella, Phaeodactylum* as well as cyanobacteria (blue-green algae) and diatoms such as *Nitzschia palea.*

The microbial cell may also be a protozoa, e.g. a member of the groups Amoebae, Sporozoa, Ciliates, and Flagellates. Representative protozoa include *Toxoplasma* species e.g. *Toxoplasma gondii, Plasmodium* species such as *Plasmodium falciparum, Plasmodium vivax, Plasmodium malariae. Trypanosoma* species e.g. *Trypanosoma brucei, Trypanosoma cruzi, Leishmania* species such as *Leishmania major*; and *Entamoeba* species such as *Entamoeba histolytica.*

Preferably the microbial cell is selected from following genera: *Citrobacter, Enterobacter, Escherichia, Hafnia, Serratia, Yersinia, Peptostreptococcus, Bacteriodes, Pseudomonas, Legionella, Staphylococcus, Enterococcus, Streptococcus, Klebsiella, Candida, Proteus, Burkholderia, Fusobacterium* and *Mycobacterium*, for instance *Staphylococcus aureus, Staphylococcus epidermidis, Legionella pneumophila, Candida albicans, Pseudomonas aeruginosa, Burkholderia cepacia* and *Streptococcus Pyogenes.*

In a further aspect, the invention provides a nucleic acid molecule encoding a peptide as defined above in respect of the oligopeptidic compound of the invention (namely a peptide having or comprising:
  (i) all or part of the amino acid sequence of SEQ ID NO: 1 or 40; or
  (ii) an amino acid sequence having at least 85% sequence identity to SEQ ID NO:1 or 40; or
  (iii) an amino acid sequence which is all or part of the reverse sequence of SEQ ID NO: 1 (namely all or part of SEQ ID NO: 2:or 41) or which is the reverse sequence of an amino acid sequence having at least 85% sequence identity to SEQ ID NO:1 or 40). Also provided is the complement of such a nucleic acid molecule. In a preferred embodiment, the nucleic acid molecule also encodes a cell penetrating peptide as defined above.

The nucleic acid molecule of the invention preferably comprises at least 30 nucleotides and preferably no more than 800 nucleotides, more preferably no more than 700, 650, 600, 550, 500, 450, 400, 350, 300, 250, 200, 150, 100 or 50. The nucleic acid molecule is preferably an isolated molecule.

A further aspect relates to a vector comprising a nucleic acid molecule as defined herein. The vector may also contain further elements typically found in a vector such as an origin of replication, a selectable marker such as antibiotic resistance, and/or a multiple cloning site. The vector may further be an expression vector, and may comprise further elements, e.g. transcriptional and/or translational control or regulatory elements for expression of the nucleic acid molecules. Such control elements, e.g., promoters, ribosome binding sites, enhancers, terminators etc. are well known and widely described in the art.

The vector may for example be a plasmid or a virus, preferably it is selected from a retrovirus, an adenovirus and an adenovirus-associated virus.

In another aspect, there is provided a recombinant host cell containing a nucleic acid molecule and/or vector as described above. The host cell may be an animal cell, for example a mammalian cell, e.g. a rat, murine or human cell, or it may be a microbial cell e.g. a bacterial cell.

By "recombinant" is meant that the nucleic acid molecule and/or vector has been introduced into the host cell.

In a further aspect, there is provided a pharmaceutical composition comprising an oligopeptidic compound as defined herein, a nucleic acid molecule as defined herein and/or a vector as defined herein, together with a pharmacologically (or pharmaceutically) acceptable excipient.

The excipient may include any excipients known in the art, for example any carrier or diluent or any other ingredient or agent such as buffer, antioxidant, chelator, binder, coating, disintegrant, filler, flavour, colour, glidant, lubricant, preservative, sorbent and/or sweetener etc.

The excipient may be selected from, for example, lactic acid, dextrose, sodium metabisulfate, benzyl alcohol, polyethylene glycol, propylene glycol, microcrystalline cellulose, lactose, starch, chitosan, pregelatinized starch, calcium carbonate, calcium sulfate, dextrates, dextrin, dextrose, dibasic calcium phosphate dihydrate, tribasic calcium phosphate, magnesium carbonate, magnesium oxide, maltodextrin, mannitol, powdered cellulose, sodium chloride, sorbitol and/or talc.

The oligopeptidic compounds may thus be delivered by different routes, depending on the condition it is desired to treat or prevent, and/or the effect it is desired to achieve, the patient being treated etc. Thus, for example the route of delivery or mode of administration may be selected to provide a systemic or local effect. Thus, for example, the oligopeptidic compounds may be administered to the subject such that they may be systemically delivered, for example via an oral or parenteral route of administration. Alternatively, and in some cases preferably, the oligopeptidic compounds may be delivered or administered locally to the site of infection or cancer, e.g. locally to a tumour. Thus, for example, it may be delivered topically or by direct administration e.g. by injection or infusion, or inhalation etc. to the site of the cancer (e.g. tumour), depending of course on the site of the cancer (tumour). Local administration is preferred in the treatment of cancer.

The pharmaceutical composition may be provided in any form known in the art, for example as a tablet, capsule, coated tablet, liquid, suspension, tab, sachet, implant, inhalant, powder, pellet, emulsion, lyophilisate, effervescent, spray, salve, emulsion, balm, plaster or any mixtures thereof. It may be provided e.g. as a gastric fluid-resistant preparation and/or in sustained action form. It may be a form suitable for oral, parenteral, topical, rectal, genital, subcutaneous, transurethral, transdermal, intranasal, intraperitoneal, intramuscular and/or intravenous administration and/or for administration by inhalation.

The pharmaceutical composition can be in a form suitable for liposomal administration, so liposomes containing the pharmaceutical composition can be provided. When liposomes are used, it may no be necessary to include a further excipient, so also provided are liposomes containing an oligopeptidic compound as defined herein, a nucleic acid molecule as defined herein and/or a vector as defined herein.

A further aspect of the invention provides a method of combating cancer and/or microbial infection, particularly bacterial infection, said method comprising administering (particularly administering an effective amount of) an oligopeptidic compound as defined herein, or a nucleic acid molecule as defined herein, to a subject in need thereof.

In another aspect, there is provided an oligopeptidic compound as defined herein, or a nucleic acid molecule as defined herein, for use in therapy, particularly for use in combating cancer and/or microbial infection, particularly bacterial infection.

In another aspect, there is provided the use of an oligopeptidic compound as defined herein, or a nucleic acid molecule as defined herein, in the manufacture of a medicament for use in combating cancer and/or microbial infection, particularly bacterial infection.

The term "combating" as used herein includes both therapeutic treatment and prevention. More particularly therefore the invention provides methods and uses for treating cancer, for example in the treatment of tumours, and/or combating microbial infection, particularly bacterial infection.

The oligopeptidic compounds (including constructs) according to the invention thus have a therapeutic utility in the treatment or management of cancer and/or microbial infections. They may thus be used as anti-cancer, or more particularly as anti-tumour, and/or anti-microbial, more particularly anti-bacterial, agents.

The oligopeptidic compounds may thus be used in the treatment of any condition (used broadly herein to include any disease or disorder or any clinical situation) which would benefit from the cytotoxic effect of the compounds of the present invention. The oligopeptidic compounds accordingly find utility in any therapy (or treatment) which targets cells, and particularly cancer cells, e.g. tumour cells, and/or microorganisms, particularly bacteria.

The term "treatment" as used herein refers broadly to any effect or step (or intervention) beneficial in the management of a clinical condition. Treatment may include reducing, alleviating, ameliorating, slowing the development of, or eliminating the condition or one or more symptoms thereof, which is being treated, relative to the condition or symptom prior to the treatment, or in any way improving the clinical status of the subject. A treatment may include any clinical step or intervention which contributes to, or is a part of, a treatment programme or regimen.

"Prevention" or "prophylaxis" may include delaying, limiting, reducing or preventing the condition or the onset of the condition, or one or more symptoms thereof, for example relative to the condition or symptom prior to the administration of the compound. Prophylaxis thus explicitly includes both absolute prevention of occurrence or development of the condition, or symptom thereof, and any delay in the onset or development of the condition or symptom, or reduction or limitation on the development or progression of the condition or symptom.

Treatment according to the invention thus includes killing, inhibiting or slowing the growth of cells, or the increase in size of a body or population of cells (e.g. in a tissue, tumour or growth), reducing cell number or preventing spread of cells (e.g. to another anatomic site), reducing the size of a cell growth etc. The term "treatment" does not imply cure or complete abolition or elimination of cell growth, or a growth of cells.

The treatment of all types of cancers, including e.g. solid tumours and haematological cancers is included. The term "cancer" is therefore used broadly herein to include any neoplastic condition; malignant, pre-malignant or non-malignant. Representative types of cancer include cervical cancer, uterine cancer, ovarian cancer, pancreatic cancer, kidney cancer, gallbladder cancer, liver cancer, head and neck cancer, squamous cell carcinoma, gastrointestinal cancer, breast cancer, prostate cancer, testicular cancer, lung cancer, non-small cell lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer (e.g. astrocytoma, glioblastoma, medulloblastoma), neuroblastoma, sarcomas, colon cancer, rectum cancer, stomach cancer, anal cancer, bladder cancer, pancreatic cancer, endometrial cancer, plasmacytoma, lymphomas, retinoblastoma, Wilm's tumor, Ewing sarcoma, melanoma and other skin cancers.

Mention may be made also of sinus tumours, urethral and genito-urinary cancers, oesophageal cancer, myeloma, endocrine cancers, osteosarcoma, angiosarcoma, and fibrosarcoma, and any tumour of the peripheral or central nervous systems, malignant or benign, including gliomas and neuroblastomas.

Cancers of particular interest include brain, lung, breast, and colon cancer and melanoma.

As shown in the examples below, the compounds of the invention may have cytotoxic effects, particularly against cancer cells, or tumours, and/or against microbial cells, particularly bacteria.

More particularly, the compounds may be able selectively to target cancer cells. In other words the compounds of the invention are selective towards cancer cell and consequently they may have no or minimal effects on normal (non-cancer) cell. In this way advantageously undesirable cytotoxic effects on non-cancerous cells may be avoided. The compounds of the present invention therefore preferably exhibit selectivity towards cancer cells. Such cells can be within a solid tumour, or can be metastatic cells. The compounds of the invention preferably do not exhibit cytotoxicity towards non-cancerous cells.

Further in the context of cancer therapy, the compounds of the invention are preferably effective in improving or extending survival, for example as assessed in an experimental animal model, e.g. in an animal in which a tumour has been induced or into which a tumour or tumour cells have been introduced. Such an animal model is described in the examples below. Further, the compounds are preferably effective in inhibiting tumour growth, e.g. in eradicating tumours or reducing tumour size or arresting or reducing the growth of a tumour, for example in an animal model as discussed above. Alternatively or additionally, the compounds are also preferably effective in preventing or reducing the spread of a tumour, or the metastatic potential of a tumour. Again this may be assessed in an animal model as discussed above.

The compounds of the invention may cause lysis and/or apoptosis of cancer cells. The Examples below demonstrate that both lytic effects and apoptotic effects were observed when compounds according to the invention were applied to various cell types. Thus, the compounds of the invention may cause lysis of cancer (tumour) cells. Lysis occurs as a result of cellular membrane disintegration, which results in cell death. Methods of determining cell lysis are known to those skilled in the art. The Examples below illustrate how this could be carried out.

Alternatively or additionally the compounds of the invention may cause apoptosis of cancer cells. Apoptosis is the process of programmed cell death (PCD) that may occur in multicellular organisms. Programmed cell death involves a series of biochemical events leading to a characteristic cell morphology and death; including blebbing, changes to the cell membrane such as loss of membrane asymmetry and attachment, cell shrinkage, nuclear fragmentation, chromatin condensation, and chromosomal DNA fragmentation. Experiments to determine whether or not a cell is undergoing, or has undergone, apoptosis are well known in the art (and see Examples below). The compounds of the invention may be lytic and/or apoptotic towards cancer cells, preferably both.

In a preferred aspect of the invention, the oligopeptidic compounds of the invention are cytotoxic against bacteria, that is to say bacteriocidal. Lysis of various types of bacteria by compounds of the invention is demonstrated in the Examples.

The compounds of the invention may be used in the treatment or prevention of infection by any microorganism, including any of the microorganisms listed above, but preferably bacterial, including any of the bacteria listed above. In particular, the infection may be a pathogen infection. Infections caused by *Citrobacter, Enterobacter, Escherichia, Hafnia, Serratia, Yersinia, Peptostreptococcus, Bacteriodes, Pseudomonas, Legionella, Staphylococcus, Enterococcus, Streptococcus, Klebsiella, Candida, Proteus, Burkholderia, Fusobacterium* and *Mycobacterium*, for instance, *Staphylococcus aureus, Staphylococcus epidermidis, Legionella pneumophila, Candida albicans, Pseudomonas aeruginosa, Burkholderia cepacia* and *Streptococcus Pyogenes* are of note.

The infection may be acute, or alternatively chronic, e.g. an infection that has persisted for at least 5 or at least 10 days, particularly at least 20 days, more particularly at least 30 days, most particularly at least 40 days.

In one embodiment, this aspect of the invention may comprise a step in which the subject is diagnosed as a candidate that is at risk of developing an infection or that would benefit from having an existing infection treated.

Included is the treatment of septicaemia, septic shock, sepsis, meningitis, or poisoning by microbial toxins, e.g. cholera toxin and botulinum toxin, as well as the treatment of more localised infections, e.g. of particular sites, tissues or organs.

An infection can occur in any subject but some subjects will be more susceptible to infection than others. Subjects who are susceptible to infection include, but are not limited to, subjects whose epithelial and/or endothelial barrier is weakened or compromised, subjects whose secretion-based defences to microbial infection have been abrogated, disrupted, weakened or undermined, and subjects who are immunocompromised, immunodeficient or immunosuppressed (i.e. a subject in whom any part of the immune system is not working normally, or is working sub-normally, in other words in whom any part of the immune response, or an immune activity is reduced or impaired, whether due to disease or clinical intervention or other treatment, or in any way).

Representative examples of subjects who are susceptible to infection include, but are not limited to, subjects with a pre-established infection (e.g. with bacteria, viruses, fungi or parasites such as protozoa), especially subjects with HIV, subjects with sepsis and subjects with septic shock; subjects with immunodeficiency, e.g. subjects preparing for, undergoing or recovering from chemotherapy and/or radiotherapy, organ (e.g. bone marrow, liver, lung, heart, heart valve, kidney, etc.) transplant subjects (including autograft, allograft and xenograft patients), subjects with AIDS; subjects resident in a healthcare institution, e.g. hospital, especially subjects in intensive care or critical care (i.e. those units concerned with the provision of life support or organ support systems to patients); subjects suffering from trauma; subjects with burns, subjects with acute and/or chronic wounds; neonatal subjects; elderly subjects; subjects with cancer, especially those with cancers of the immune system (e.g. leukaemias, lymphomas and other haematological cancers); subjects suffering from auto-immune conditions such as rheumatoid arthritis, diabetes mellitus type I, Crohn's disease, especially those undergoing immunosuppression treatment for those diseases; subjects with reduced or abrogated epithelial or endothelial secretion (e.g. mucous, tears, saliva) and/or secretion clearance (e.g. subjects with poorly functioning cilia on mucosal tissue and/or patients with hyperviscous mucous (e.g. smokers and subjects with COPD, bronchitis, cystic fibrous, emphysema, lung cancer, asthma, pneumonia or sinusitis) and subjects fitted with a medical device.

Thus, subjects in whom infections may particularly be combated according to the present invention include patients who are impaired, whether due to poor perfusion, repetitive trauma, poor nutrition, poor oxygenation or white cell dysfunction.

Of particular note are subjects that have undergone physical trauma. The trauma itself might cause a weakening in or compromisation of an epithelial and/or endothelial barrier of the subject or the subject may become immunocompromised in response to the trauma (a shock response). The term "trauma" refers broadly to cellular attack by foreign bodies and/or physical injury of cells. Included among foreign bodies are microorganisms, particulate matter, chemical agents, and the like. Included among physical injuries are mechanical injuries; thermal injuries, such as those resulting from excessive heat or cold; electrical injuries, such as those caused by contact with sources of electrical potential; and radiation damage caused, for example, by prolonged, extensive exposure to infrared, ultraviolet or ionizing radiations.

Also of particular note are subjects that have a burn. Any burn, in particular a severe burn, has a significant impact on the integrity of the epithelial and/or endothelial barrier of the subject and the subject will often become immunocompromised in response to the burn (a shock response).

Typical burn-causing agents are extremes of temperature (e.g. fire and liquids and gases at extreme temperature), electricity, corrosive chemicals, friction and radiation. The extent and duration of exposure, together with the intensity/strength of the agent, result in burns of varying severity. Scalding (i.e. trauma associated with high temperature liquids and/or gases) is considered to be a burn.

The invention may also be used for the treatment or prevention of infection of wounds, whether acute or chronic. Acute wounds are wounds that proceed orderly through the three recognised stages of the healing process (i.e. the inflammatory stage, the proliferative stage and the remodelling phase) without a protracted timecourse. Chronic wounds, however, are those wounds that do not complete the ordered sequence of biochemical events of the healing process because the wound has stalled in one of the healing stages. Commonly, chronic wounds are stalled in the inflammatory phase. A chronic wound may be defined as a wound that has not healed within at least 40 days, particularly at least 50 days, more particularly at least 60 days, most particularly at least 70 days. Wounds are an ideal environment for infection, particularly chronic infection, due to their lack of an epithelial barrier and the availability of substrate and surface for microbial attachment and colonisation. Problematically, infection of a wound often delays healing further and thus renders that wound more susceptible to established infection.

The compounds may thus be used to treat infections wherever they may occur in or on the body. Thus, in another embodiment, the infection may be an infection of a medical device, particularly an in-dwelling medical device.

The compounds may be used according to the present invention as oral healthcare agents, for example in the control of dental plaque, e.g. to reduce it or to prevent, reduce or delay its development, by killing the microorganisms in the plaque or inhibiting the replication or growth of said microorganisms. The alginate oligomers may also be used in the treatment and prevention of infections or infectious disease which may occur in the oral cavity, for example gingivitis and periodontitis.

The compounds of the invention can be used as a prophylactic treatment, for example to prevent, or at least minimise the risk, of infection or contamination (e.g. by a pathogen). This may be of utility the care of hospitalised patients as the risk of contracting a nosocomial infection (commonly known as hospital related/acquired infection or healthcare-associated infection), e.g. *Staphylococcus aureus*, Methicillin Resistant *Staphylococcus aureus* (MRSA), *Pseudomonas aeruginosa, Acinetobacter baumannii, Stenotrophomonas maltophilia, Clostridium difficile, Mycobacterium tuberculosis* and Vancomycin-Resistant *Enterococcus*, can be minimised with a prophylactic regime of the compounds defined herein. This aspect of the invention is also of particular utility in the care of subjects suffering from trauma, subjects with a burn and subjects with wounds, all of which, as discussed above, are more susceptible to microbial infection than a subject that is not affected similarly.

A "pharmaceutically effective" amount of the oligopeptidic compound is the amount that provides a measurable effect (e.g. cytotoxic or cytostatic effect) on the targeted cell and/or a measurable effect on the condition being targeted. Preferably it is an amount sufficient directly to kill the cell or inhibit its growth. This amount can be determined with reference to standard practices for deciding dosage amounts and the skilled man will be able to detect evidence of successful treatment from his experience and with the aid of routine tests available to him.

The subject may be any human or non-human animal subject, but more particularly may be a vertebrate, e.g. an animal selected from mammals, birds, amphibians, fish and reptiles. The animal may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, cod, haddock, sea bass and carp. Veterinary uses of the invention are thus covered. The subject may be viewed as a patient. Preferably the subject is a human.

As noted above, in terms of the anti-microbial effects of the compounds the invention is not limited to medical uses (i.e. the treatment or prevention of infections) and non-medical uses are also covered, for example to combat microbial contamination or colonisation (e.g. at, in, or on inanimate sites or locations) e.g. for disinfection or cleaning purposes.

Thus more generally the invention includes a method for inhibiting the viability and/or growth of a microbial cell (or alternatively put, a microorganism, said method comprising contacting said cell (or microorganism) with an oligopeptidic compound as hereinbefore defined. In particular, the method is an in vitro method. Thus, this aspect may alternatively be viewed as a method for inhibiting the viability and/or growth of a microorganism, or of combating microbial contamination or colonisation, at an inanimate site, said method comprising contacting said site with an oligopeptidic compound as hereinbefore defined. "Combating" as used in this context includes inhibiting (i.e. reducing or preventing) microbial contamination or colonisation, as well as treating an existing contamination or colonisation.

The term "contacting" encompasses any means of delivering the compound to the microorganism or site, whether directly or indirectly, and thus any means of applying the compound to the microorganism or site or exposing the microorganism or site to the compound e.g. applying the compound directly to the microorganism or site.

More particularly the microorganism or site will be contacted with an effective amount of the alginate compound, more particularly an amount of the compound effective directly to inhibit the viability of (e.g. to kill) the microorganism or to inhibit directly the growth of the microorganism.

The site or location of the microorganism is not restricted. The microorganism may be present on a surface. The site is not limited and includes any site on or in which a microorganism may occur or which may be exposed to microbial contact or contamination. Thus particularly included are (sites on) machinery, notably industrial machinery, or medical equipment or any site exposed to an aquatic environment (e.g. marine equipment, or ships or boats or their parts or components), or any site exposed to any part of the environment, e.g. pipes or on buildings. Such inanimate sites exposed to microbial contact or contamination include in particular any part of: food or drink processing, preparation, storage or dispensing machinery or equipment, air conditioning apparatus, industrial machinery, e.g. in chemical or biotechnological processing plants, storage tanks, medical or surgical equipment and cell and tissue culture equipment. Any apparatus or equipment for carrying or transporting or delivering materials is susceptible to microbial contamination. Such surfaces will include particularly pipes (which term is used broadly herein to include any conduit or line). Representative inanimate or abiotic surfaces include, but are not limited to food processing, storage, dispensing or preparation equipment or surfaces, tanks, conveyors, floors, drains, coolers, freezers, equipment surfaces, walls, valves, belts, pipes, air conditioning conduits, cooling apparatus, food or drink dispensing lines, heat exchangers, boat hulls or any part of a boat's structure that is exposed to water, dental waterlines, oil drilling conduits, contact lenses and storage cases.

As noted above, medical or surgical equipment or devices represent a particular class of surface on which microbial contamination may form. This may include any kind of line, including catheters (e.g. central venous and urinary catheters), prosthetic devices e.g., heart valves, artificial joints, false teeth, dental crowns, dental caps and soft tissue implants (e.g. breast, buttock and lip implants). Any kind of implantable (or "in-dwelling") medical device is included (e.g. stents, intrauterine devices, pacemakers, intubation tubes, prostheses or prosthetic devices, lines or catheters). An "in-dwelling" medical device may include a device in which any part of it is contained within the body, i.e. the device may be wholly or partly in-dwelling.

The site can also be food, for example, beef, poultry, pork, vegetables, fruits, fish, shellfish, combinations thereof, and the like, personal hygiene products, toiletries, cosmetics etc; chemical or industrial products and reagents etc; clinical, scientific or industrial waste materials etc. Thus the compounds may be used as preservative or decontaminating agents in materials, especially liquids and solutions.

In certain advantageous embodiments of the invention the compounds may be used in conjunction or combination with a second or further anti-microbial agent (hereinafter "further anti-microbial agent").

In the context of a medical use, such an anti-microbial agent may be any clinically-useful anti-microbial agent and particularly an antibiotic or an antiviral or antifungal agent. In the context of non-clinical uses, the anti-microbial agent may again be any anti-microbial agent used for such purposes, e.g. any disinfectant or antiseptic or cleaning or sterilising agent. The agents may be used separately, or together in the same composition, simultaneously or sequentially or separately, e.g. at any desired time interval.

The choice of anti-microbial agent will of course need to be appropriate for the treatment or use concerned, but for instance anti-microbial agents, e.g. antibiotics, antifungals, antivirals, antiseptics may be used and/or sterilising conditions such as irradiation (e.g. UV, X-ray, gamma) extremes of temperature, and extremes of pH.

The further anti-microbial agent may conveniently be applied before, simultaneously with or following the compound. Conveniently the further anti-microbial agent is applied at substantially the same time as the compound or afterwards. To optimise the anti-microbial effect of the further anti-microbial agent it can be given (e.g. administered or delivered) repeatedly at time points appropriate for the agent used. The skilled person is able to devise a suitable dosage or usage regimen. In long term treatments the compound can also be used repeatedly. The frequency required will depend on the microorganism, site, disease, utility, composition and the anti-microbial used etc. and the skilled person is able to optimise the dosage or usage patterns to optimise results.

Similarly and analogously, in the context of the cancer therapies described herein, the compounds of the invention may be used in combination or conjunction with other anti-cancer agents, for example chemotherapy agents or anti-neoplastic agent or any agent which may be indicated for an oncological or haematological indication.

Thus, the compounds of the invention may be used in combination with other therapeutic agents, for example to be administered together, in a single pharmaceutical formulation or composition, or separately (i.e. for separate, sequential or simultaneous administration). Thus, the compounds of the invention may be combined with a second (or further) therapeutically active agent, e.g. in a pharmaceutical kit or as a combined ("combination") product.

Thus a further aspect of the present invention provides a product containing an oligopeptidic compound or nucleic acid molecule as defined herein and a second active agent (e.g. anti-cancer or anti-microbial agent) as a combined preparation for separate, simultaneous or sequential use (e.g. application to a microorganism or site and/or administration to a subject) in inhibiting the viability and/or growth of a cancer or microbial cell, or more particularly in treating cancer or combating microbial infection or microbial contamination or colonisation of a site, or indeed any of the uses described or defined herein.

The skilled person will be well aware of suitable methods for introducing the oligopeptidic compound or nucleic acid molecule into cells. By way of example, a few suitable methods are briefly discussed below. As discussed in detail above, peptide-mediated methods of delivery can be used, notably cell penetrating peptides (CPPs), which as discussed above, are short, in some cases polycationic, sequences which can facilitate cellular uptake of peptides, proteins or nucleotide molecules which contain CPPs or to which CPPs are linked, for example by enhancing uptake into endosomes of mammalian cells. Microencapsulation provides a simple and cost-effective way to enclose bioactive materials within a semi-permeable polymeric membrane for the purpose of protecting the bioactive materials and releasing the enclosed substances or their products in a controlled fashion. In photochemical internalisation (PCI) both the molecule of interest and a photosensitising compound are taken up by the cell into a lysosome or an endosome. The cells are then exposed to light of suitable wavelengths to activate the photosensitising compound, causing the photosensitising compound to disrupt the membrane of the lysosome or endosome, thereby releasing the molecule of interest into the cytosol of the cell.

Other methods include microinjection, red blood cell ghost-mediated fusion, liposome fusion, osmotic lysis of pinosomes, scrape loading, electroporation, calcium phosphate and virus-mediated transfection and the use of copolymeric carriers.

Chitosan and water-soluble chitosan derivatives, in particular glycol chitosan, are emerging as the drug carriers of choice because of their biocompatibility and biodegradability in vivo. A preferred example is glycol chitosan hydrophobically modified with 5 β-cholanic acid.

The "oligopeptidic compound" of the invention may incorporate one or more, e.g. at least 1, 2, 3, 4 or 5 amino acids which possess a side chain that is not coded for by the standard genetic code, termed herein "non-coded amino acids". These may be selected from amino acids which are formed through metabolic processes such as ornithine or taurine, and/or artificially modified amino acids such as 9H-fluoren-9-ylmethoxycarbonyl (Fmoc), (tert)-(B)utyl (o)xy (c)arbonyl (Boc), 2,2,5,7,8-pentamethylchroman-6-sulphonyl (Pmc) protected amino acids, or amino acids having the benzyloxycarbonyl (Z) group.

In vitro and/or in vivo stability of the oligopeptidic compounds of the invention may be improved or enhanced through the use of stabilising or protecting means known in the art, for example the addition of protecting or stabilising groups, incorporation of amino acid derivatives or analogues or chemical modification of amino acids. Such protecting or stabilising groups may for example be added at the N and/or C-terminus. An example of such a group is an acetyl group and other protecting groups or groups which might stabilise a peptide are known in the art.

The Examples below show that modified oligopeptidic compounds of the invention that have been modified to include D-amino acids and/or wherein the reverse sequence of SEQ ID NO:1 is utilised may retain the anti-cancer and/or anti-microbial activity of the invention.

Thus, in one embodiment the oligopeptidic compounds of the invention comprise only amino acids having the L-configuration, but in a further embodiment one or more amino acids having the D configuration are present. The oligopeptidic compound may contain at least 1, 2, 3, 4, 5, 6, 7, 8, 9, 10, 11 or 12 D-amino acids. Preferably, the oligopeptidic compound contains all D-amino acids. Thus, included particularly are inverso oligopeptidic compounds or inverso analogues of the oligopeptidic compounds of the invention (and more particularly inverso peptides).

As specifically set out above, also included are "retro" oligopeptidic compounds (or retro peptides) in which the residues (e.g. amino acid residues) are assembled in opposite direction to the parental or reference compound (e.g. peptide). Thus, included are compounds in which, for example, the sequence of SEQ ID NO: 1 or SEQ ID NO: 40 is reversed. The reverse sequences are set out in SEQ ID NO.s 2 and 41 respectively.

Retro-inverso oligopeptidic compounds include D-amino acids in reverse (opposite) order to the parental or reference compound sequence. A retro-inverso analogue thus has reversed termini and reversed order of e.g. peptide bonds, while approximately maintaining the topology of the side chains as in the parental or reference sequence.

The compounds of the invention may include partial inverso, retro or retro-inverso sequences. In a preferred embodiment the compound is inverso and in a further preferred embodiment the sequence is or comprises EIYRKY-IAKAVRLTK (SEQ ID NO. 2). In a further preferred embodiment the compound is retro-inverso, i.e. is composed of or comprises D-amino acids of the sequence of SEQ ID NO. 2 or SEQ ID NO:41.

By "oligopeptidic compound" is meant a compound which is composed of amino acids or equivalent subunits, which are linked together by peptide or equivalent bonds. Thus, the term "oligopeptidic compound" includes peptides and peptidomimetics.

By "equivalent subunit" is meant a subunit which is structurally and functionally similar to an amino acid. The backbone moiety of the subunit may differ from a standard amino acid, e.g. it may incorporate one or more nitrogen atoms instead of one or more carbon atoms.

By "peptidomimetic" is meant a compound which is functionally equivalent or similar to a peptide and which can adopt a three-dimensional structure similar to its peptide counterparts, but which is not solely composed of amino acids linked by peptide bonds. A preferred class of peptidomimetics are peptoids, i.e. N-substituted glycines. Peptoids are closely related to their natural peptide counterparts, but they differ chemically in that their side chains are appended to nitrogen atoms along the molecule's backbone, rather than to the α-carbons as they are in amino acids.

Peptidomimetics typically have a longer half life within a patient's body, so they are preferred in embodiments where a longer lasting effect is desired. This can help reduce the frequency at which the composition has to be re-administered. However, for bio-safety reasons a shorter half life may be preferred in other embodiments; in those embodiments peptides are preferred.

Most preferably, the oligopeptidic compound is a peptide. The oligopeptidic compound may incorporate di-amino acids and/or β-amino acids. Most preferably, the oligopeptidic compound consists of α-amino acids.

The prefix "oligo" is used to designate a relatively small number of subunits such as amino acids, i.e. less than 200, preferably less than 100, 90, 80, 70 60 or 50 subunits. The oligopeptidic compound of the invention may thus comprise at least 7 and no more than 200 subunits. Preferably, it comprises at least 8, 9, 10, 11, 12, 13, 14, 15, 16, 17, 18, 19, 20, 21, 22, 23 or 24 subunits. Alternatively defined it comprises no more than 50, 45, 40, 35, 30, 29, 28, 27, 26 or 25 subunits. Representative subunit ranges thus include 10-40, 10-35, 10-30, 10-25, 10-20, 10-15, 10-12 etc, 10-20 and 10-30 being preferred. Other representative ranges include 15-50, 15-45, 15-40, 15-35 and 15-30, more particularly 20-50, 20-45, 20-40, 20-30, 25-50, 25-45, 25-40, 25-35, 25-32 and 25-30.

The oligopeptidic compounds of the present invention may comprise or consist of an amino acid sequence having at least 85%, 86%, 87%, 88%, 89%, 90%, 91%, 92%, 93%, 94%, 95%, 96%, 97%, 98%, 99% or 100% identity with the sequence set out in SEQ ID NO 1, 2, 40 or 41.

Sequence identity may be assessed by any convenient method. However, for determining the degree of sequence identity between sequences, computer programs that make multiple alignments of sequences are useful, for instance Clustal W (Thompson et al., (1994) Nucleic Acids Res., 22: 4673-4680). Programs that compare and align pairs of sequences, like ALIGN (Myers et al., (1988) CABIOS, 4: 11-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are also useful for this purpose. Furthermore, the Dali server at the European Bioinformatics institute offers structure-based alignments of protein sequences (Holm (1993) J. Mol. Biol., 233: 123-38; Holm (1995) Trends Biochem. Sci., 20: 478-480; Holm (1998) Nucleic Acid Res., 26; 316-9).

Multiple sequence alignments and percent identity calculations may be determined using the standard BLAST parameters, (using sequences from all organisms available, matrix Blosum 62, gap costs: existence 11, extension 1). Alternatively, the following program and parameters may be used: Program; Align Plus 4, version 4.10 (Sci Ed Central Clone Manager Professional Suite). DNA comparison: Global comparison, Standard Linear Scoring matrix, Mismatch penalty=2, Open gap penalty=4, Extend gap penalty=1. Amino acid comparison; Global comparison, BLOSUM 62 Scoring matrix.

Thus included in the scope of the invention are variants of the stated or given sequences, as long as the variant oligopeptidic compound retains the functional activity of the parent i.e. the variants are functionally equivalent, in other words they have or exhibit an activity of the parent compound as defined herein (e.g. an inhibitory effect on the growth and/or viability of cancer and/or microbial cells, cytotoxic activity, anti-tumour or anti-bacterial activity etc. Such variants may comprise amino acid substitutions, additions or deletions (including truncations at one or both ends) of the parent sequence e.g. of one or more e.g. 1 to 6 amino acids.

Also included are functionally-equivalent derivatives in which one or more of the amino acids are chemically derivatised, e.g. substituted with a chemical group.

Thus, the oligopeptidic compounds of the invention can comprise fragments of SEQ ID NO:1, 2, 40 or 41 provided that the compound retains the required activity. Fragments of SEQ ID NO:1 or 2 may for example be from 7 to 14 residues in length, e.g. 12 or 13 residues in length. Fragments of SEQ ID NO: 40 or 41 may be from 13 to 26 residues in length, e.g. 13, 14, 15, 16 or 17 to 26 residues in length.

As described in the Examples below, the peptide of SEQ ID NO: 40 is a strongly cationic peptide having a net charge at pH 7.0 of 12 and a high isoelectric point (pI) of 12.4. It is preferred that compounds of the invention, and hence their functionally equivalent variants, including their fragments, have similar properties. In other words, it is preferred that the variants, including fragments, retain the physicochemical properties of the parent compound. Such properties include in particular that they are cationic. The peptide of SEQ ID NO. 40 has an α-helical structure. In certain embodiments, compounds of the invention may have an α-helical structure, but this is not an essential feature; in other embodiments the compounds may have a β-sheet structure, or may have another or an un-ordered structure e.g. a coil, or the compound may have a composite structure with domains of different structure.

In preferred representative embodiments, the compounds of the invention, including functionally equivalent variants and fragments of SEQ ID NOs. 1, 2, 40 or 41, may have one or more of the following properties:
at net charge at pH7.0 of 10-13, e.g. 11-12.5;
a pI of 12 to 13;
an average hydrophilicity of 0.7 to 1.0 e.g. 0.8 to 1.0;
a ratio of hydrophilic residues/total number of residues of 45-60%, e.g. 46-58%, 48-58%, or 50-56%.

The oligopeptidic compound of the invention may form part of a larger unit, e.g. it may be fused to a polypeptide to form a recombinant fusion protein or attached to a scaffold to form a peptide aptamer. Thus, fusion proteins or aptamers incorporating the oligopeptidic compound of the invention form further aspects of the present invention. Yet further aspects include pharmaceutical compositions comprising such fusions proteins or aptamers and the use of such fusions proteins or aptamers in therapy or in a method of treatment as described above.

Also contemplated is the in vitro administration of an oligopeptidic compound, nucleic acid molecule and/or a vector as defined herein to a cell or cell culture. Such in vitro methods may be used to study the cytotoxic effects of the compounds of the invention.

The invention will now be further described in the following non-limiting Examples, with reference to the following Figures in which.

Figure 10:
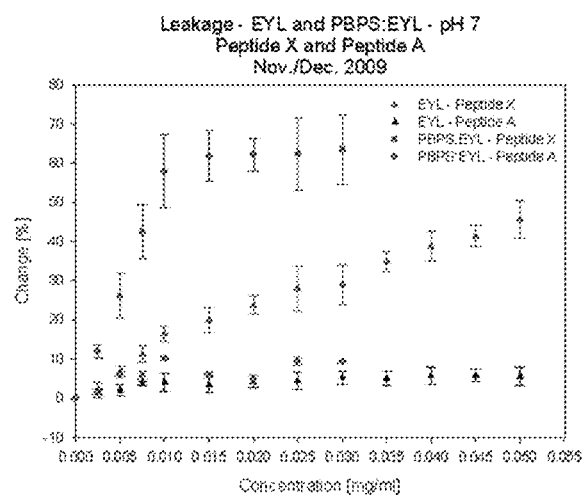

FIG. 10 shows 200 nm liposomes that contained different compositions of phospholipids in the lipid bi-layer. The liposomes were loaded with a fluorescent dye and the dye efflux was measured after treatment of Peptide 1 (Peptide X on FIG. 10). The dye refers to a fluorophore ANTX, and a quencer, DPX, and dye release refers to % of total release with detergent (Triton x100).

Figure 11:

FIG. 11 shows time lapse confocal microscopy visualizing membrane disruption and release of ds Red from the cells at different time points. The white arrows highlight cells that suddenly lose the cytoplasmic content of ds Red caused by membrane disruption.

Figure 12:
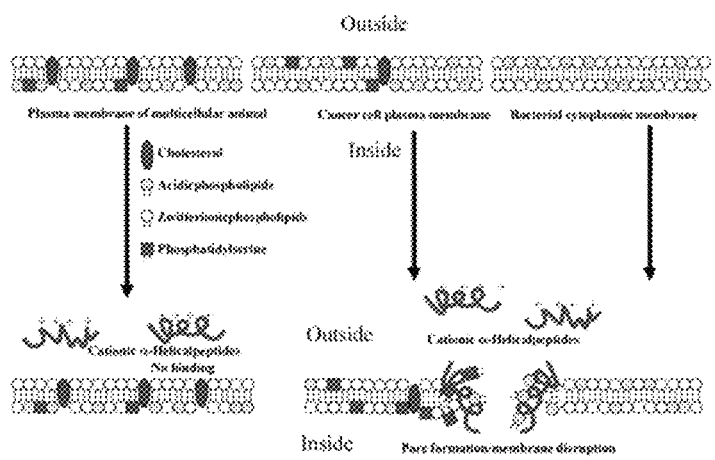

FIG. 12 shows a theoretical explanation for the observed membrane disruption effects.

Figure 13:
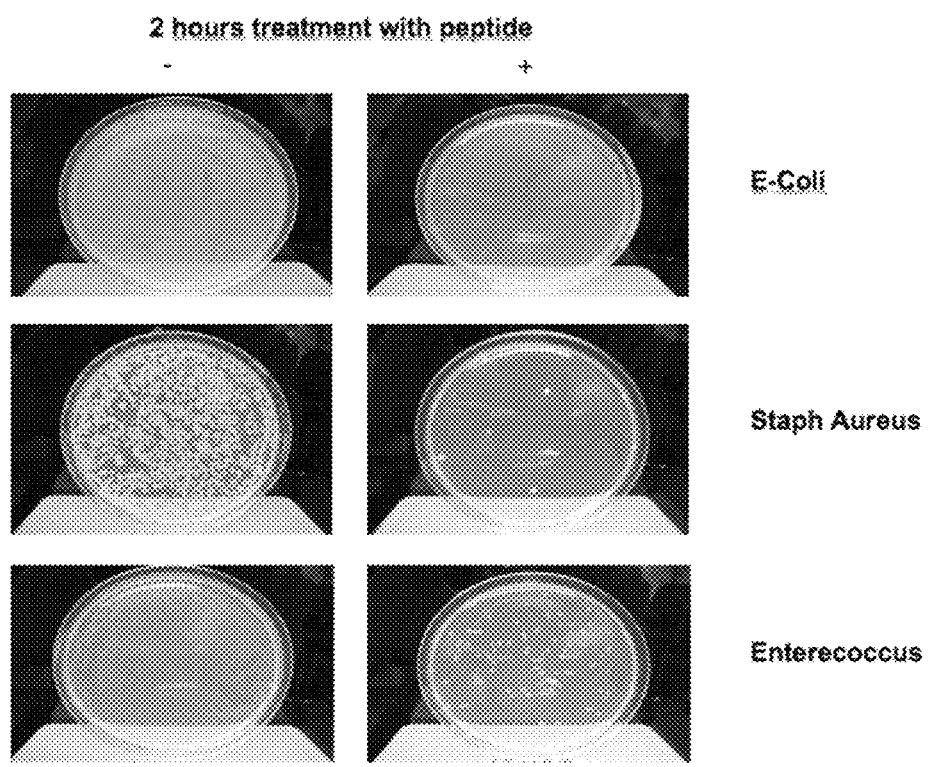

FIG. 13 shows the results on the growth of three strains of bacteria when they were incubated with and without Peptide 1 for two hours.

Figure 14:
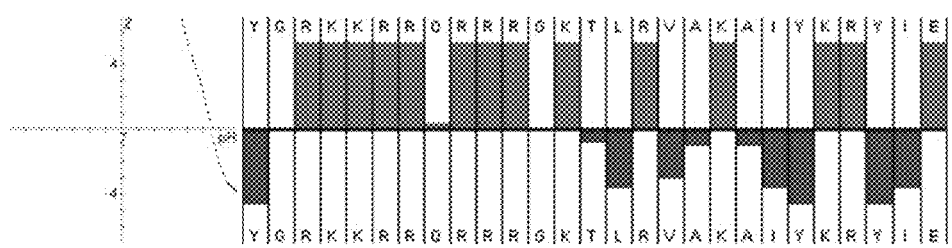

FIG. 14 shows the net charge at pH 7.0 of Peptide 1 (SEQ ID NO: 40) is 12; the isoelectric point is 12.4; the average hydrophilicity is 1; and the ratio of hydrophilic residues/total number of residues is 56%.

EXAMPLES

Example 1

Initial Design and Screening of 96 Peptides and Effects on Cancer Cell Survival and Morphology Peptide Design and Production Possible conserved elements and active sites from known tumor suppressors (see Table 2) were identified by using the search engines Expasy and Swissprot. 96 peptides were identified. The TAT sequence was attached at the N-terminal for intracellular delivery. Peptides were synthezised at Cambridge Peptides (Cambridge, UK) and Genscript (NJ, USA). All were amidated and acetylated. Synthezised peptides were dissolved in water to a final concentration of 1 mg/ml.

Cell Culture

The cell lines U87, MCF7, SF295. T47D and 4T1 were obtained from the tumor bank at the University of Bergen, Norway. Fibroblasts were obtained from healthy donors. All cell lines were grown in DMEM (Sigma, St. Louis, Mo., USA) containing 10% fetal bovine serum supplemented with NEAA, 100 U/ml Pen/Strep and 400 µM L-glutamine, all from Cambrex (East Rutherford, N.J., USA). In all experiments $1 \times 10^4$ cells were distributed into a 96-well plate.

Cell Survival

Figure 1:
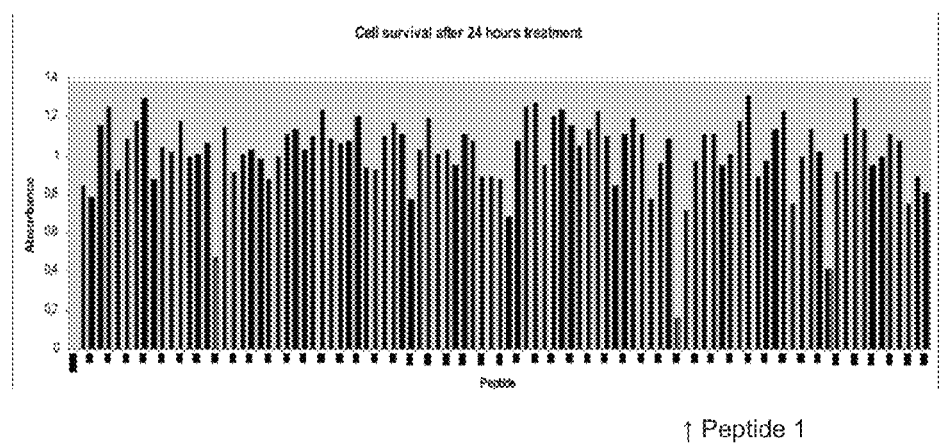
FIG. 1 shows the effect on cell survival after 24 hours treatment with the 96 synthetic peptides designed for screening. The peptide of SEQ ID NO. 40, identified as "Peptide 1", resulted in the lowest absorbance, indicating the lowest cell survival (Peptide 1 is indicated by an arrow next to the shortest bar on the graph of FIG. 1).

The results of cell survival in the initial screen of the glioma cell line u87 following 24 hours culture with the 96 peptides that were identified are shown in FIG. 1. Three peptides were shown to have a marked negative effect on the viability of the cancer cells. Of these Peptide 1 (SEQ ID NO. 40) was selected for further study.

"Peptide 1" corresponds to the peptide sequence of SEQ ID NO:1 with the HIV-TAT sequence of SEQ ID NO. 36 at its N-terminal end.

Cell Morphology

Figure 2:
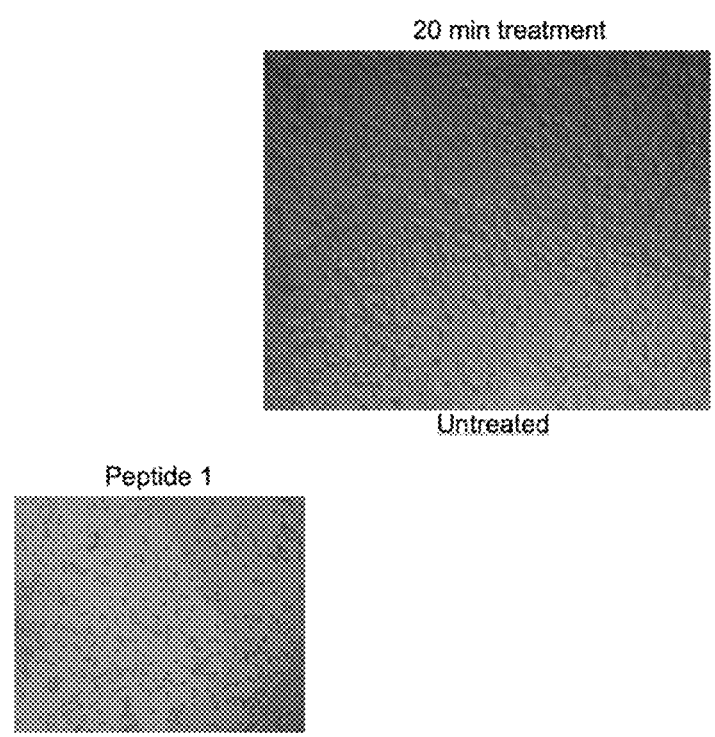
FIG. 2 shows the morphological effects determined by light microscopy on cells following 20 minutes of culture with three of the 96 peptides.

The cell morphology following 20 minutes of culture with three of the 96 peptides was determined by light microscopy and time-lapse microscopy, and the results are shown in FIG. 2. The results show a massive contraction of cellular processes and the appearance of pyknotic cells, indicating cell death.

Peptide Stabilization

Figure 3:
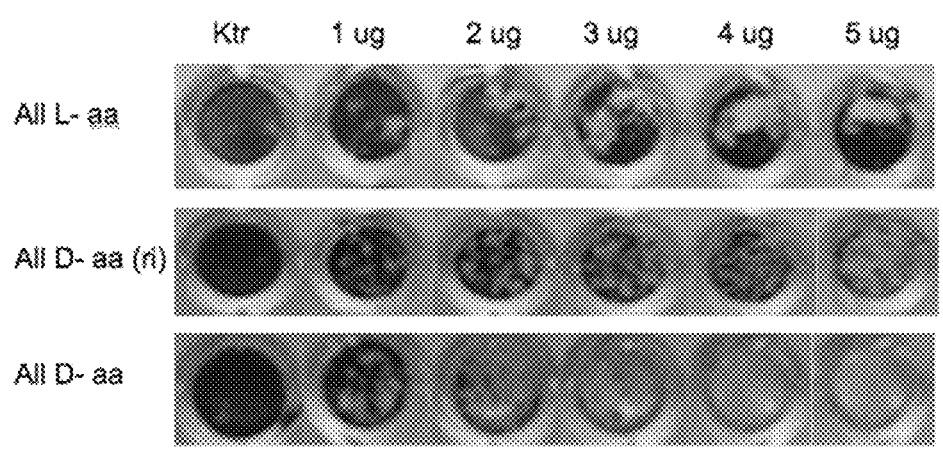
FIG. 3 shows the effects on cells in monolayer culture of Peptide 1 in all L-amino acid form (SEQ ID NO. 40), Peptide 1 in retro-inverso (ri) form, that is all D-amino acids in reverse sequence (SEQ ID NO. 41) and Peptide 1 (SEQ ID NO. 40) in all D-amino acid form.

A main problem with peptides in general is that they are subjected to proteolytic degradation, particularly by proteases present in the serum. The inventors therefore designed a strategy for stabilizing the peptides by substituting the L-amino acids with D-amino acids. The studies show that the peptides did not lose their effect in serum supplemented media. In fact, the peptides were also resistant for proteolytic degradation in trypsin. FIG. 3 indicates the efficacy of the substituted peptides in monolayer cultures indicating that the substituted peptides even work better than the original peptides.

Example 2

In Vitro Effects of Peptide 1 on Cancer Cells

Cell Viability, Comparison Between Normal Cells and Cancer Cell Lines In Vitro.

Figure 4:
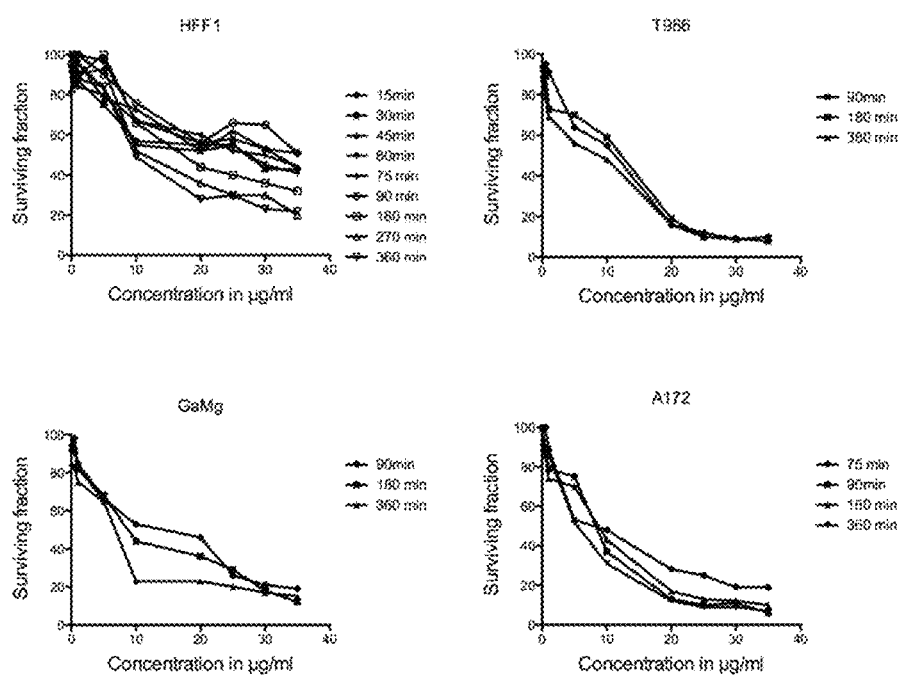
FIG. 4 shows MTT analyses of Peptide 1 on HFF1 (human foreskin fibroblasts) T986 (neuroblastoma), GaMG (glioblastoma) and A172 (glioblastoma) at different peptide concentrations administered at different time points. A lower survival fraction is observed for the tumour cell lines compared to the HFF1 cells.

MTT Cell Viability Assay:

MTT (Thiazolyl Blue Tetrazolium Bromide) may be used in measurement of cell proliferation in studies that traditionally use incorporation of radioisotopes as a measurement of cell division. MTT is a yellowish solution and is converted to water-insoluble MTT-formazan of dark blue colour by mitochondrial dehydrogenases of living cells. The blue crystals are solubilized with acidifies isopropanol and the intensity is measured colorimetrically at a wavelength of 570 nm (protocol for the MTT assay was used according to the manufacturer's instructions). Using a MTT cell viability assay, a comparison was made between normal human forskin fibroblasts (HFF1) and three cancer cell lines T986 (neuroblastoma cells), GaMG (glioblastoma), and A172 (glioblastoma). At a concentration of 20 µg/ml the surviving fraction was between 19 and 43% after an exposure of Peptide 1 for 90 minutes. In comparison, the surviving fraction for the normal HFF1 cells was 58% which indicates a stronger effect of the peptide on the cancer cells (see FIG. 4).

Comparison of Cellular Viability Using the Molecular Probes (Live/Dead Kit).

The LIVE/DEAD® Viability/Cytotoxicity kit employs a fluorescent dye to assess mammalian cell viability. Calcein AM and ethidium homodimer-1 (EthD-1) are found to be optimal dyes for this purpose. We cells are distinguished from dead cells by the presence of intracellular esterase activity, determined by enzymatic conversion of non-fluorescen calcein AM to intensely fluorescent calcein. Calcein, which is a polyanionic dye, is well retained inside living cells producing an intense uniform green fluorescence. EthD-1 is excluded by intact membranes of viable cells, but it will enter cells with damaged cell membrane and bind to nucleic acids, producing a bright red fluorescence in dead cells. The protocol for using the live/dead kit is supplied by the manufacturer.

To quantify the cytotoxic action of Peptide 1, 20 000 cells were placed in 24 well multiwell dishes. After 48 hrs, peptide 1 was added to the wells at concentrations ranging from, 0.1 to 3 5 µg/ml. After 1-3-6 hrs the cellular viability was assessed using the Molecular Probes LIVE/DEAD kit. The cells were briefly washed in phosphate buffered saline (PBS) whereupon 10 µM EthD-1 and 5 µM calcein was added to the wells. The cells were then incubated in the tissue culture incubator at 37° C. for 30 min.

The cells were then observed using an inverted fluorescence microscope (Nikon Eclipse 2000E, Tokyo, Japan)

equipped with FITC (green fluorescence) and TRITC (red fluorescence) filter optics. The fluorescent cells were then photographed at 100× magnification. The proportion of viable cells (cells with green fluorescence) and the proportion of dead cells (red fluorescence) where then assessed by counting 100 cells.

Figure 5:
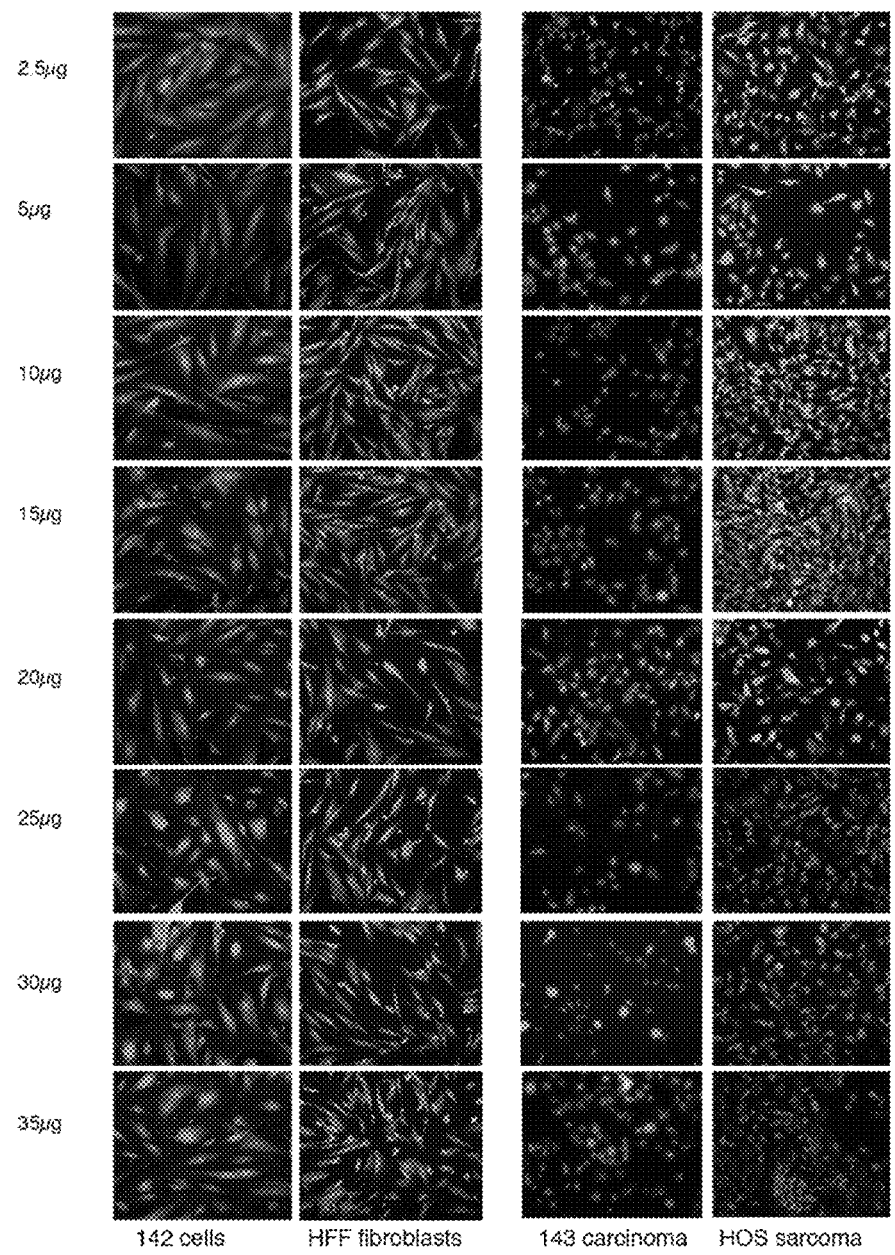
FIG. 5 shows the results from the LIVE/DEAD viability assay of two normal cell lines (142 cells and HFF1 cells) as well as two cancer cell lines, 143 carcinoma cells and a HOS sarcoma cell line) cells treated with 2.5- to 30 µg/ml of peptide respectively. Compared to the normal cell lines a strong cytotoxic action was observed for the two cancer cell lines.

The control cells showed a confluent monolayer containing cells with a green fluorescence. No red fluorescent cells were observed indicating 100% viability (FIG. 5). The same fluorescence was observed in cells receiving 0.1, 1, and 5 µg/ml of peptide. However some red cells were observed in monolayers receiving 10 µg/ml of peptide indicating a slight cytotoxic action at this concentration. In contrast cells receiving 15 µg/ml of peptide showed a fairly large proportion of dead cells (FIG. 5). The monolayers that received 30 µg/ml of peptide showed a strong cytotoxic action indicated by nearly 100% dead cells (see FIG. 5).

The percentages of live and dead cells at different concentrations are shown in Table 3. The lytic action of the peptide occurred after 1 hour and no further changes were observed at 3 and 6 hours.

Morphology

Figure 6:
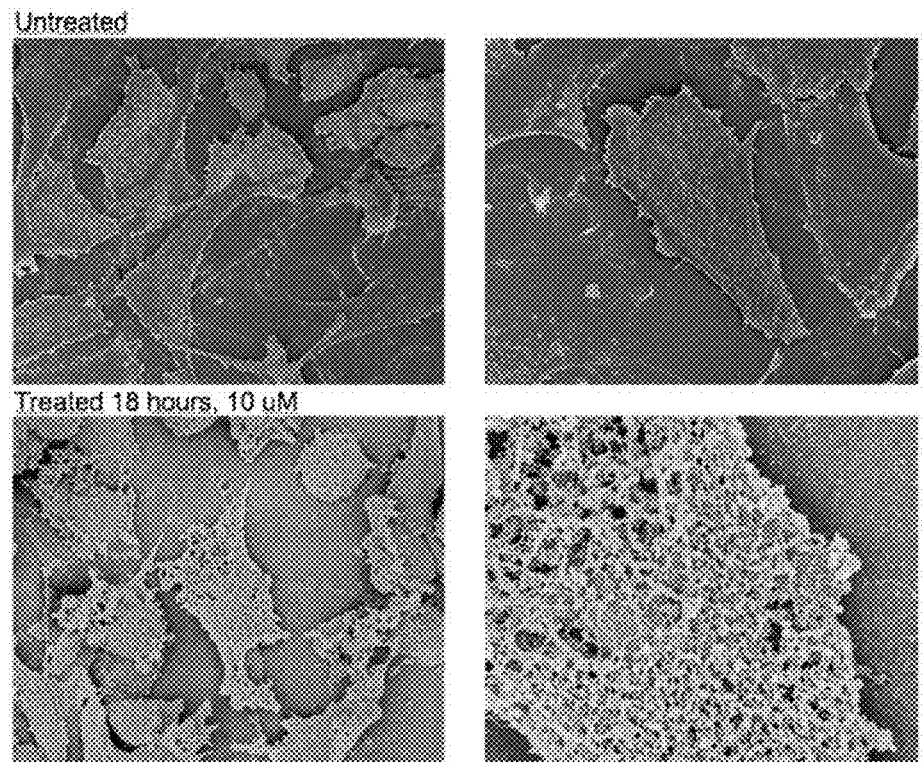
FIG. 6(A) shows high resolution scanning electron microscopy images of cells following treatment with Peptide 1. (B) shows labelled N-terminal part of the peptides with fluorescein thiocyanate
Figure 6:
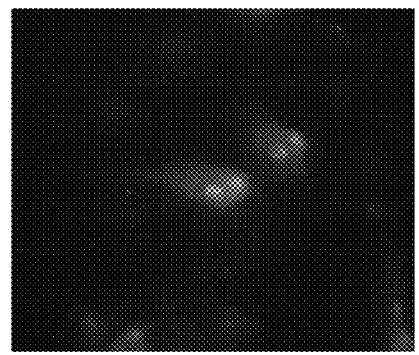

High resolution scanning electron microscopy showed a total disintegration of the plasma membrane after peptide treatment indicating that the peptide excerts a strong cytolytic action affecting the plasma membrane (FIG. 6A). By detailed morphological analyses in vitro, there was also some evidence of cellular fragmentation which indicates induction of apoptosis. We therefore labelled the N-terminal part of the peptides with fluorescein thiocyanate (FITC) and treated them in vitro. Immunofluorescence shortly after treatment indicated that the peptides also accumulated in the nucleus. There is therefore some evidence that the peptides also trigger apoptosis through interactions with nuclear proteins. As seen in FIG. 6B, Peptide 1 also accumulates in the nucleus. Based on the morphological observations done in tissue culture there is also some evidence that the peptide also triggers apoptosis.

Example 3

In Vivo Effects of Peptide 1 on Cancer Cells

The 4T1 mammary carcinoma is a transplantable tumour cell line that is highly tumourigenic and invasive and, unlike most tumor models, can spontaneously metastasize from the primary tumour in the mammary gland to multiple distant sites including lymph nodes, blood, liver, lung, brain, and bone. The 4T1 tumour has several characteristics that make it a suitable experimental animal model for human mammary cancer. First, tumour cells are easily transplanted into the mammary gland so that the primary tumour grows in the anatomically correct site. Second, as in human breast cancer, 4T1 metastatic disease develops spontaneously from the primary tumour. Also, the progressive spread of 4T1 metastases to the draining lymph nodes and other organs is very similar to that of human mammary cancer.

$1 \times 10^6$ 4T1 cells were injected subcutaneously into 12 female BALBc mice. 6 animals in the treatment group and 6 animals in the control group which received a scrambled peptide sequence. When the tumours had reached a size of 0.8 cm, (after 10 days) the tumours received three local injections of 400 µg peptide administered in 100 µl. Total concentration of peptide administered was 1200 µg. The tumours were then recorded with calipers every 4th day.

Tumour Growth.

Figure 7:
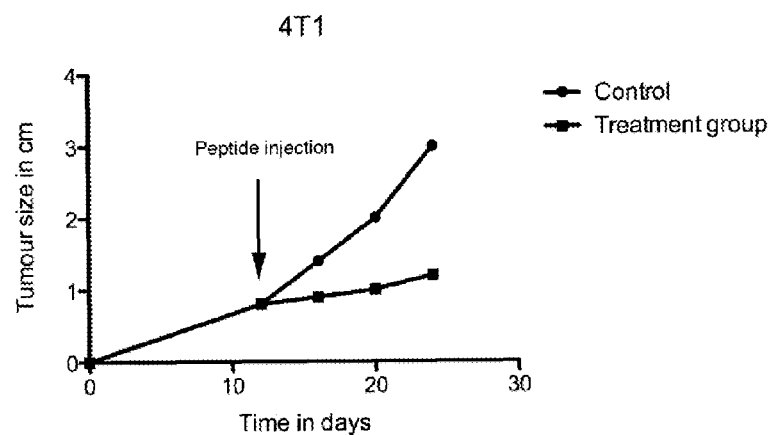
FIG. 7 shows that local injection of Peptide 1 into 4T1 tumours in mice induces a strong growth-Inhibitory effect of the 4T1 tumour.

As shown in FIG. 7, the local injection of peptide into the 4T1 tumour induced a strong growth-inhibitory effect of the 4T1 tumour in vivo. The data points represents average values from six animals in the control group and treatment group.

Animal Survival.

Figure 8:
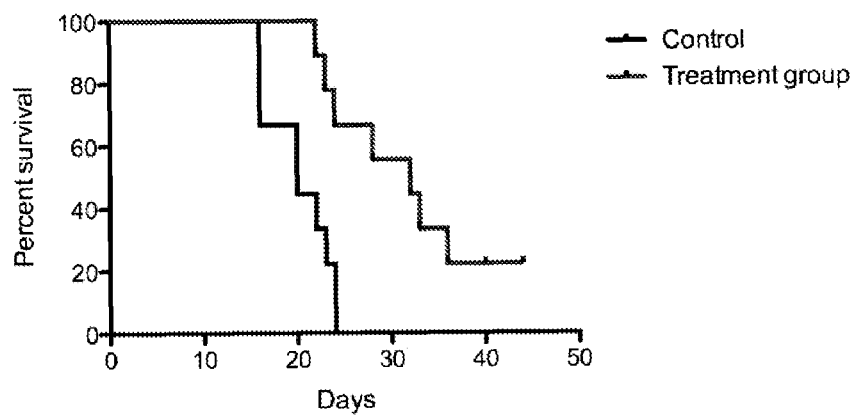
FIG. 8 shows the results of Kaplan Meier survival experiments, comparing treated and untreated animals subcutaneously injected with 4T1 cancer cells. The animals were sacrificed when they showed signs of systemic disease, based on a severe tumour burden.
Figure 9:
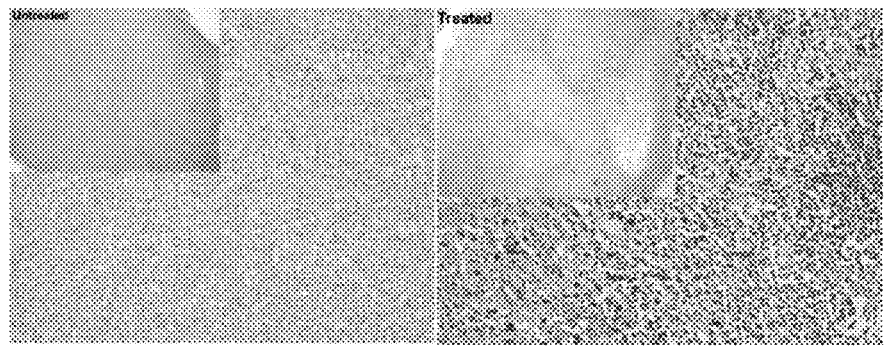
FIG. 9 shows histological analysis of the tumours from the Kaplan Meier survival experiments.

We performed Kaplan Meier survival experiments, comparing treated and untreated animals subcutaneously injected with 4T1 cancer cells. The animals were sacrificed when the animals showed signs of systemic disease, based on a severe tumour burden. As seen in FIG. 8, the treatment group had a significant survival advantage compared to the untreated group. The tumours were at collected for histological analysis. Excised tumours were fixed in 4% buffered formaldehyde. Paraffin-embedded 5-µm sections were stained with H&E. Cell cultures were fixed in 4% PFA and imaged under a Nikon Eclipse TE2000-E fluorescence microscope (Nikon, Tokyo, Japan). As seen in FIG. 9, a severe necrosis was observed following massive cell death, indicating a strong cytotoxic action of the peptide.

Example 4

In Vitro and In Vivo Membrane Disruption Experiments 200 nm liposomes were made that contained different compositions of phospholipids in the lipid bi-layer. The liposomes were loaded with a fluorescent dye and the dye efflux was measured after treatment with Peptide 1 (Peptide X on FIG. 10). The dye refers to a fluorophore ANTX, and a quencer, DPX, and dye release refers to % of total release with detergent (Triton x100). As shown in FIG. 10, Peptide 1 had a severe function as a vesicle disruptor, in particular if the phospholipids were negatively charged (PBPS:EYL; blue symbols; 50.5 (for half maximal effect)=8.5 µg/ml; 2.46 µM). The peptide had also some effects on neutral (polar) phospholipids (EYL: green symbols) but this effect was less than on the negatively charged phospholipids. A control peptide (peptide A) was used as a reference that has the same size but different sequence. Peptide A had no effects at the concentrations studied.

4T1 mammary carcinoma cells was stably transfected, using a lentiviral vector, to express the fluorescent marker dsRed. The transfected cells will accumulate dsRed in the cytoplasm and can be easily visualized in the fluorescent microscope (see FIG. 11). The cells were then exposed to 20 µg/ml of Peptide 1 and time-lapse confocal microscopy was performed during a 3 hr period. This study allows a direct visualization of membrane disruption in cancer cells.

FIG. 12 shows a theoretical explanation for the observed effects. It is known that cancer cells frequently have cell membranes that are negatively charged compared to normal cells. A cationic peptide will have little effect on normal cells which have cellular membranes that are less charged compared to cancer cell membranes, which have more acidic phospholipids and phospatidylserine at the outer surface, most likely due to increased flip-flop activity in the phospholipid bi-layer. Peptide 1 most likely binds to negatively charged phospholipids creating holes in the phospholipid bi-layer. Since many bacterial cell membranes are negatively charged, we also assessed the action of the peptide on various bacterial strains.

Example 5

Effects of Peptide 1 on Bacteria

Peptide 1 also shows bacteriocidal activity, killing bacteria within two hours. The strains tested was *E. coli, S. aureus* and

*Enterococcus*. This indicates that the peptide also shows lytic activity both against gram positive as well as gram negative bacterias. FIG. 13 shows the results when the strains of bacteria mentioned above were incubated with and without Peptide 1 for two hours.

Example 6

Physical Properties of Peptide 1

It was determined that the net charge at pH7.0 of Peptide 1 is 12; the isoelectric point is 12.4; the average hydrophilicity is 1; and the ratio of hydrophilic residues/total number of residues is 56%. Peptide 1 is thus strongly cationic and has a high isoelectric point. The results are shown in FIG. 14.

TABLE 2

Known tumour suppressors used in peptide screening

PTEN
p15
p12
p27
par-4
P53BP1
PML
ATM
chd5
apc
smad4
puma
retinoblastoma
NF1
patched
Numb
Axin
WT
SMAD2
SMAD3
P16

TABLE 3

Percentages of Live and Dead Cells at Different Concentrations, Comparison Between Two Normal Cell Lines (142 and HFF1) and Two Cancer Cell Lines (143 Carcinoma and HOS Sarcoma)

| Peptide concentration | Proportion of living cells (%) | | | |
|---|---|---|---|---|
| | Normal Cells | | Tumour cells | |
| | 142 | HFF1 | 143 Carcinoma | HOS Sarcoma |
| 2.5 µg/ml | 99 | 100 | 90 | 90 |
| 5 µg/ml | 100 | 99 | 90 | 91 |
| 10 µg/ml | 99 | 100 | 89 | 88 |
| 15 µg/ml | 90 | 95 | 75 | 78 |
| 20 µg/ml | 97 | 98 | 50 | 35 |
| 25 µg/ml | 89 | 90 | 45 | 8 |
| 30 µg/ml | 90 | 88 | 30 | 10 |
| 35 µg/ml | 90 | 89 | 29 | 2 |

Discussion of the Examples

The experiments show that Peptide 1, and modified peptides based upon it have anti-tumoural effects on a variety of cancer cell lines in vitro as well as in viva. Moreover, the peptides show very little toxicity on human fibroblasts in vitro as well by intraperitoneal injection in mice. In fact, no toxicity is seen by injecting 1000 µg of the peptides subcutaneously in 18 gr, nod-scid mice. The peptides arrest the growth of a number of cancer cell lines in vitro, whereas normal cells are less affected by the same concentrations. By direct peptide injection in solid tumours in mice, severe necrosis is observed after 24 hrs with a subsequent growth inhibition. Moreover, this will lead to an extensive animal survival compared to untreated animals. Scanning electron microscopy, as well as functional studies show that the peptide affects the cancer cell plasma membranes causing membrane disruption. Moreover, the peptide also translocates to the nucleus triggering apoptotic mechanisms in cancer cells. Thus, Peptide 1, and modifications thereof, which have novel sequences, represent therapeutic molecules that inhibit tumour growth of various cancers (for example, brain, lung, breast and colon). The results also show by a simple manipulation, that the peptides can be stabilized (made resistant) towards proteolytic degradation which further increases their potential as anti-tumour compounds. Moreover, the results show that the peptides exert bacteriocidal effects on both gram-positive as well as gram negative bacteria. The peptides may therefore be used against a variety of bacterial infections in humans.

REFERENCES

1. Dunn G P, Bruce A T, Ikeda H, Old L J, Schreiber R D. Cancer immunoediting: from immunosurveillance to tumor escape. Nat Immunol 2002; 3:991-8.
2. Mocellin S, Rossi C R, Nitti D. Cancer vaccine development: on the way to break immune tolerance to malignant cells. Exp Cell Res 2004; 299:267-78.
3. Blattman J N, Greenberg P D. Cancer immunotherapy: a treatment for the masses. Science 2004; 305:200-5.
4. Boman H G. Peptide antibiotics and their role in innate immunity. Annu Rev Immunol 1995; 13:61-92.
5. Hancock R E. Peptide antibiotics. Lancet 1997; 349: 418-22.
6. Ganz T, Lehrer R I. Antimicrobial peptides of vertebrates. Curr Opin Immunol 1998; 10:41-4.
7. Zasloff M. Antimicrobial peptides of multicellular organisms. Nature 2002; 415:389-95.
8. Ohsaki Y, Gazdar A F, Chen H C, Johnson B E. Antitumor activity of magainin analogues against human lung cancer cell lines. Cancer Res 1992; 52:3534-8
9. Chen Y, Xu X, Hong S, et al. RGD-Tachyplesin inhibits tumor growth. Cancer Res 2001; 61:2434-8.
10. Street S E, Cretney E, Smyth M J. Perforin and interferon-g activities independently control tumor initiation, growth, and metastasis. Blood 2001; 97:192-7.
11. Ellerby H M, Lee S, Ellerby L M, et al. An artificially designed pore-forming protein with anti-tumor effects. J Biol Chem 2003; 278:35311-6.
12. Leuschner C, Enright F M, Gawronska B, Hansel W. Membrane disrupting lytic peptide conjugates destroy hormone dependent and independent breast cancer cells in vitro and in vivo. Breast Cancer Res Treat 2003; 78:17-27.
13. Papo N, Braunstein A, Eshhar Z, Shai Y. Suppression of human prostate tumor growth in mice by a cytolytic D-, L-amino acid peptide: membrane lysis, increased necrosis, and inhibition of prostate-specific antigen secretion. Cancer Res 2004; 64:5779-86.
14. Ganz T, Lehrer R I. Defensins, Curr Opin Immunol 1994; 6:584-9.
15. Epand R M, Vogel H J. Diversity of antimicrobial peptides and their mechanisms of action. Biochim Biophys Acta 1999; 15:1-2.
16. Shai Y. Mechanism of the binding, insertion and destabilization of phospholipid bilayer membranes by a-helical antimicrobial and cell non-selective membrane-lytic peptides. Biochim Biophys Acta 1999; 1462:

17. Tossi A, Sandri L, Giangaspero A. Amphipathic, a-helical antimicrobial peptides. Biopolymers 2000; 55:4-30.

18. Bulet P, Stocklin R, Menin L. Anti-microbial peptides: from invertebrates to vertebrates. Immunol Rev 2004; 198: 169-84.

19. Shai Y. Mode of action of membrane active antimicrobial peptides. Biopolymers 2002; 66:236-48.

20. Papo N, Shahar M, Eisenbach L, Shai Y. A novel lytic peptide composed of D, L amino acids selectively kills cancer cells in culture and in mice. J Biol Chem 2003; 278:21018-23.

21. Zwaal R F, Schroit A J. Pathophysiologic implications of membrane phospholipid asymmetry in blood cells. Blood 1997; 89:1121-32.

22. Zwaal R F, Comfurius P, Bevers E M. Surface exposure of phosphatidylserine in pathological cells. Cell Mol Life Sci 2005; 62:971-88.

23. Chen H M, Wang W, Smith D, Chan S C. Effects of the anti-bacterial peptide cecropin B and its analogs, cecropins B-1 and B-2, on liposomes, bacteria, and cancer cells. Biochim Biophys Acta 1997; 1336:171-9.

24. Chan S C, Yau W L, Wang W, Smith D K, Sheu F S, Chen H M. Microscopic observations of the different morphological changes caused by anti-bacterial peptides on *Klebsiella pneumoniae* and HL-60 leukemia cells. J Pept Sci 1998; 4:413-25.

25. Papo N, Shai Y. New lytic peptides based on the D, L amphipathic helix motif preferentially kill tumor cells compared to normal cells. Biochemistry 2003; 42:9346-54.

26. Manno S, Takakuwa Y, Mohandas N. Identification of a functional role for lipid asymmetry in biological membranes: phosphatidylserine-skeletal protein interactions modulate membrane stability. Proc Natl Acad Sci USA 2002; 99:1943-8.

27. Ellerby H M, Arap W, Ellerby L M, et al. Anti-cancer activity of targeted pro-apoptotic peptides. Nat Med 1999; 5:1032-8.

28. Baker M A, Maloy W L, Zasloff M, Jacob L S. Anticancer efficacy of magainin 2 and analogue peptides. Cancer Res 1993; 53:3052-7.

What is claimed is:

1. A method of treating a bacterial infection and/or treating a neoplastic condition, the method comprising administering to a subject in need thereof an oligopeptidic compound comprising:
   (i) the amino acid sequence YGRKKRRQRRRGKTLRVAKAIYKRYIE (SEQ ID NO: 40); or
   (ii) an amino acid sequence having at least 95% sequence identity to SEQ ID NO: 40; wherein the compound has activity in inhibiting the growth and/or viability of bacterial cells and/or neoplastic cells, and further wherein the neoplastic condition is selected from brain cancer, breast cancer, melanoma, neuroblastoma, sarcoma, colon cancer, prostate cancer and a neoplastic condition of the skin.

2. The method of claim 1, wherein the oligopeptidic compound has the sequence of SEQ ID NO: 40.

3. The method of claim 1, wherein the oligopeptidic compound comprises one or more D-amino acids.

4. The method of claim 3, wherein all the amino acids of the oligopeptidic compound are D-amino acids.

5. The method of claim 1, wherein the oligopeptidic compound has one or more of the following properties:
   a) a net charge at pH 7.0 of 10-13; b) a pI of 12 to 13; c) an average hydrophilicity of 0.7 to 1.0; and/or d) a ratio of hydrophilic residues to total number of residues of 45-60%.

6. The method of claim 1, wherein the oligopeptidic compound is cytotoxic.

7. The method of claim 1, wherein the oligopeptidic compound induces lysis and/or apoptosis of neoplastic cells.

8. The method of claim 1, wherein the oligopeptidic compound is selectively cytotoxic towards neoplastic cells.

9. The method of claim 1, wherein the neoplastic condition comprises a tumor and the size of the tumor is reduced.

10. The method of claim 1, wherein when used in the treatment of the neoplastic condition, the oligopeptidic compound is locally delivered to the site of the neoplastic condition.

11. The method of claim 1, wherein the method further comprises administering a second therapeutically active agent to the subject, wherein the second therapeutically active agent is selected from the group consisting of a chemotherapy agent, an anti-neoplastic agent, an antibiotic, an antiviral agent, and an antifungal agent.

12. The method of claim 1, wherein the bacterial infection is caused by *Staphylococcus* or by enteric or coliform bacteria.

13. The method of claim 1, wherein the bacterial infection is caused by *Staphylococcus aureus, Escherichia coli,* or an *Enterococcus*.

14. The method of claim 1, wherein the bacterial infection is caused by bacteria from a genus selected from the group consisting of *Escherichia, Staphylococcus, Enterococcus, Klebsiella, Pseudomonas,* and *Stenotrophomonas*.

15. The method of claim 14, wherein the bacteria is selected from the group consisting of *Staphylococcus aureus, Staphylococcus epidermidis, Escherichia coli, Pseudomonas aeruginosa,* and *Stenotrophomonas maltophilia*.

16. The method of claim 1, wherein the neoplastic condition of the skin is a non-malignant tumor of the skin.

17. An in vitro or ex vivo method for inhibiting the viability and/or growth of a bacterial cell, the method comprising contacting the bacterial cell with an oligopeptidic compound comprising:
   (i) the amino acid sequence YGRKKRRQRRRGKTLRVAKAIYKRYIE (SEQ ID NO: 40); or
   (ii) an amino acid sequence having at least 95% sequence identity to SEQ ID NO: 40;
   wherein the compound has activity in inhibiting the growth and/or viability of the bacterial cell.

18. An in vitro or ex vivo method for inhibiting the viability and/or growth of cells of a neoplastic condition selected from the group consisting of brain cancer cells, breast cancer cells, melanoma cells, neuroblastoma cells, sarcoma cells, colon cancer cells, prostate cancer cells, and non-malignant skin tumor cells, the method comprising contacting the cells of the neoplastic condition with an oligopeptidic compound comprising:
   (i) the amino acid sequence YGRKKRRQRRRGKTLRVAKAIYKRYIE (SEQ ID NO: 40); or
   (ii) an amino acid sequence having at least 95% sequence identity to SEQ ID NO: 40;
   wherein the compound has activity in inhibiting the growth and/or viability of the cells of the neoplastic condition.

* * * * *

```
                         SEQUENCE LISTING

<160> NUMBER OF SEQ ID NOS: 41

<210> SEQ ID NO 1
<211> LENGTH: 15
<212> TYPE: PRT
<213> ORGANISM: Artificial sequence
<220> FEATURE:
<223> OTHER INFORMATION: Artifically synthesized peptide

<400> SEQUENCE: 1

Lys Thr Leu Arg Val Ala Lys Ala Ile Tyr Lys Arg Tyr Ile Glu
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Artifically synthesized reverse peptide

<400> SEQUENCE: 2

Glu Ile Tyr Arg Lys Tyr Ile Ala Lys Ala Val Arg Leu Thr Lys
1               5                   10                  15

<210> SEQ ID NO 3
<211> LENGTH: 16
<212> TYPE: PRT
<213> ORGANISM: Artificial sequence
<220> FEATURE:
<223> OTHER INFORMATION: Artifically synthesized Penetratin peptide

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 4
```

```
Arg Arg Met Lys Trp Lys Lys
1               5

<210> SEQ ID NO 5
<211> LENGTH: 8
<212> TYPE: PRT
<213> ORGANISM: Artificial sequence
<220> FEATURE:
<223> OTHER INFORMATION: Artifically synthesized Penetratin derivative
      peptide

<400> SEQUENCE: 5

Asn Arg Arg Met Lys Trp Lys Lys
1               5

<210> SEQ ID NO 6
<211> LENGTH: 9
<212> TYPE: PRT
<213> ORGANISM: Artificial sequence
<220> FEATURE:
<223> OTHER INFORMATION: Artifically synthesized Penetratin derivative
      peptide

<400> SEQUENCE: 6

Gln Asn Arg Arg Met Lys Trp Lys Lys
1               5

<210> SEQ ID NO 7
<211> LENGTH: 10
<212> TYPE: PRT
<213> ORGANISM: Artificial sequence
<220> FEATURE:
<223> OTHER INFORMATION: Artifically synthesized Penetratin derivative
      peptide

<400> SEQUENCE: 7

Phe Gln Asn Arg Arg Met Lys Trp Lys Lys
1               5                   10

<210> SEQ ID NO 8
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 8

Arg Arg Glu Lys Trp Lys Lys
1               5

<210> SEQ ID NO 9
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 9

Arg Arg Gln Lys Trp Lys Lys
1               5

<210> SEQ ID NO 10
<211> LENGTH: 7
<212> TYPE: PRT
<213> ORGANISM: Artificial sequence
```

```
<220> FEATURE:
<223> OTHER INFORMATION: Artificially synthesized Penetratin derivative
      peptide

<400> SEQUENCE: 10

Lys Arg Met Lys Trp Lys Lys
1               5

<210> SEQ ID NO 11
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 11

Arg Lys Met Lys Trp Lys Lys
1               5

<210> SEQ ID NO 12
<211> LENGTH: 7
<212> TYPE: PRT
<213> ORGANISM: Artificial sequence
<220> FEATURE:
<223> OTHER INFORMATION: Artifically synthesized Penetratin derivative
      peptide
<220> FEATURE:
<221> NAME/KEY: MOD_RES
<222> LOCATION: (3)..(3)
<223> OTHER INFORMATION: Orn

<400> SEQUENCE: 12

Arg Arg Xaa Lys Trp Lys Lys
1               5

<210> SEQ ID NO 13
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 13

Arg Arg Met Lys Gln Lys Lys
1               5

<210> SEQ ID NO 14
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 14

Arg Arg Met Lys Trp Phe Lys
1               5

<210> SEQ ID NO 15
<211> LENGTH: 7
<212> TYPE: PRT
<213> ORGANISM: Artificial sequence
<220> FEATURE:
<223> OTHER INFORMATION: Artifically synthesized Penetratin derivative
      peptide
<220> FEATURE:
<221> NAME/KEY: MOD_RES
```

```
<222> LOCATION: (2)..(2)
<223> OTHER INFORMATION: Orn

<400> SEQUENCE: 15

Arg Xaa Arg Lys Trp Lys Lys
1               5

<210> SEQ ID NO 16
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 16

Arg Arg Met Trp Lys Lys Lys
1               5

<210> SEQ ID NO 17
<211> LENGTH: 7
<212> TYPE: PRT
<213> ORGANISM: Artificial sequence
<220> FEATURE:
<223> OTHER INFORMATION: Artifically synthesized Penetratin derivative
      peptide

<400> SEQUENCE: 17

Arg Arg Met Lys Lys Trp Lys
1               5

<210> SEQ ID NO 18
<211> LENGTH: 16
<212> TYPE: PRT
<213> ORGANISM: Artificial sequence
<220> FEATURE:
<223> OTHER INFORMATION: Artifically synthesized D-penetratin peptide

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 18
<212> TYPE: PRT
<213> ORGANISM: Artificial sequence
<220> FEATURE:
<223> OTHER INFORMATION: Artifically synthesized Pegelin peptide

<400> SEQUENCE: 19

Arg Gly Gly Arg Leu Ser Tyr Ser Arg Arg Phe Ser Thr Ser Thr
1               5                   10                  15

Gly Arg

<210> SEQ ID NO 20
<211> LENGTH: 13
<212> TYPE: PRT
<213> ORGANISM: Human immunodeficiency virus

<400> SEQUENCE: 20

Gly Arg Lys Lys Arg Arg Gln Arg Arg Arg Pro Pro Gln
1               5                   10

<210> SEQ ID NO 21
<211> LENGTH: 11
<212> TYPE: PRT
```

<213> ORGANISM: Human immunodeficiency virus

<400> SEQUENCE: 21

Tyr Gly Arg Lys Lys Arg Arg Gln Arg Arg Arg
1               5                   10

<210> SEQ ID NO 22
<211> LENGTH: 33
<212> TYPE: PRT
<213> ORGANISM: Artificial sequence
<220> FEATURE:
<223> OTHER INFORMATION: Artificially synthesized VP22 peptide

<400> SEQUENCE: 22

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Val
            20                  25                  30

Asp

<210> SEQ ID NO 23
<211> LENGTH: 18
<212> TYPE: PRT
<213> ORGANISM: Artificial sequence
<220> FEATURE:
<223> OTHER INFORMATION: Artificially synthesized MAP peptide

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 27
<212> TYPE: PRT
<213> ORGANISM: Artificial sequence
<220> FEATURE:
<223> OTHER INFORMATION: Artificially synthesized Transportan peptide

<400> SEQUENCE: 24

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 25
<211> LENGTH: 21
<212> TYPE: PRT
<213> ORGANISM: Artificial sequence
<220> FEATURE:
<223> OTHER INFORMATION: Artificially synthesized Transportan-10 peptide

<400> SEQUENCE: 25

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 26
<211> LENGTH: 30
<212> TYPE: PRT
<213> ORGANISM: Artificial sequence
<220> FEATURE:
<223> OTHER INFORMATION: Artificially synthesized KALA peptide -continued

<400> SEQUENCE: 26

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 27
<211> LENGTH: 21
<212> TYPE: PRT
<213> ORGANISM: Artificial sequence
<220> FEATURE:
<223> OTHER INFORMATION: Artificially synthesized Pep-1 peptide

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 21
<212> TYPE: PRT
<213> ORGANISM: Artificial sequence
<220> FEATURE:
<223> OTHER INFORMATION: Artificially synthesized Pep-2 peptide

<400> SEQUENCE: 28

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 29
<211> LENGTH: 27
<212> TYPE: PRT
<213> ORGANISM: Artificial sequence
<220> FEATURE:
<223> OTHER INFORMATION: Artificially synthesized MPG peptide

<400> SEQUENCE: 29

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 30
<211> LENGTH: 19
<212> TYPE: PRT
<213> ORGANISM: Artificial sequence
<220> FEATURE:
<223> OTHER INFORMATION: Artificially synthesized Vectocell peptide

<400> SEQUENCE: 30

Val Lys Arg Gly Leu Lys Leu Arg His Val Arg Pro Arg Val Thr Arg
1               5                   10                  15

Met Asp Val

<210> SEQ ID NO 31
<211> LENGTH: 14
<212> TYPE: PRT
<213> ORGANISM: Artificial sequence
<220> FEATURE:
<223> OTHER INFORMATION: Artificially synthesized Vectocell peptide

```
<400> SEQUENCE: 31

Ser Arg Arg Ala Arg Arg Ser Pro Arg His Leu Gly Ser Gly
1               5                   10

<210> SEQ ID NO 32
<211> LENGTH: 16
<212> TYPE: PRT
<213> ORGANISM: Artificial sequence
<220> FEATURE:
<223> OTHER INFORMATION: Artifically synthesized Vectocell peptide

<400> SEQUENCE: 32

Leu Arg Arg Glu Arg Gln Ser Arg Leu Arg Arg Glu Arg Gln Ser Arg
1               5                   10                  15

<210> SEQ ID NO 33
<211> LENGTH: 22
<212> TYPE: PRT
<213> ORGANISM: Artificial sequence
<220> FEATURE:
<223> OTHER INFORMATION: Artifically synthesized Vectocell peptide

<400> SEQUENCE: 33

Gly Ala Tyr Asp Leu Arg Arg Glu Arg Gln Ser Arg Leu Arg Arg
1               5                   10                  15

Arg Glu Arg Gln Ser Arg
            20

<210> SEQ ID NO 34
<211> LENGTH: 29
<212> TYPE: PRT
<213> ORGANISM: Artificial sequence
<220> FEATURE:
<223> OTHER INFORMATION: Artifically synthesized Wr-T rtansporter
      peptide

<400> SEQUENCE: 34

Lys Glu Thr Trp Trp Glu Thr Trp Trp Thr Glu Trp Trp Thr Glu Trp
1               5                   10                  15

Ser Gln Gly Pro Gly Arg Arg Arg Arg Arg Arg Arg
            20                  25

<210> SEQ ID NO 35
<211> LENGTH: 7
<212> TYPE: PRT
<213> ORGANISM: Artificial sequence
<220> FEATURE:
<223> OTHER INFORMATION: Artifically synthesized R7 peptide

<400> SEQUENCE: 35

Arg Arg Arg Arg Arg Arg Arg
1               5

<210> SEQ ID NO 36
<211> LENGTH: 12
<212> TYPE: PRT
<213> ORGANISM: Human immunodeficiency virus

<400> SEQUENCE: 36

Tyr Gly Arg Lys Lys Arg Arg Gln Arg Arg Gly
1               5                   10

<210> SEQ ID NO 37
<211> LENGTH: 8
```

```
<212> TYPE: PRT
<213> ORGANISM: Artificial sequence
<220> FEATURE:
<223> OTHER INFORMATION: Artifically synthesized R8 peptide

<400> SEQUENCE: 37

Arg Arg Arg Arg Arg Arg Arg Arg
1               5

<210> SEQ ID NO 38
<211> LENGTH: 11
<212> TYPE: PRT
<213> ORGANISM: Artificial sequence
<220> FEATURE:
<223> OTHER INFORMATION: Artifically synthesized R11 peptide

<400> SEQUENCE: 38

Arg Arg Arg Arg Arg Arg Arg Arg Arg Arg Arg
1               5                   10

<210> SEQ ID NO 39
<211> LENGTH: 10
<212> TYPE: PRT
<213> ORGANISM: Artificial sequence
<220> FEATURE:
<223> OTHER INFORMATION: Artifically synthesized QSR8 peptide

<400> SEQUENCE: 39

Gln Ser Arg Arg Arg Arg Arg Arg Arg Arg
1               5                   10

<210> SEQ ID NO 40
<211> LENGTH: 27
<212> TYPE: PRT
<213> ORGANISM: Artificial sequence
<220> FEATURE:
<223> OTHER INFORMATION: Artifically synthesized peptide

<400> SEQUENCE: 40

Tyr Gly Arg Lys Lys Arg Arg Gln Arg Arg Arg Gly Lys Thr Leu Arg
1               5                   10                  15

Val Ala Lys Ala Ile Tyr Lys Arg Tyr Ile Glu
            20                  25

<210> SEQ ID NO 41
<211> LENGTH: 27
<212> TYPE: PRT
<213> ORGANISM: Artificial sequence
<220> FEATURE:
<223> OTHER INFORMATION: Artifically synthesized reverse peptide

<400> SEQUENCE: 41

Glu Ile Tyr Arg Lys Tyr Ile Ala Lys Ala Val Arg Leu Thr Lys Gly
1               5                   10                  15

Arg Arg Arg Gln Arg Arg Lys Lys Arg Gly Tyr
            20                  25
```